United States Patent [19]

Holland

[11] Patent Number: 4,511,576
[45] Date of Patent: Apr. 16, 1985

[54] ANTIDIABETIC PYRROLECARBOXYLIC ACIDS

[75] Inventor: Gerald F. Holland, Old Lyme, Conn.

[73] Assignee: Pfizer Inc., New York, N.Y.

[21] Appl. No.: 406,921

[22] Filed: Aug. 10, 1982

Related U.S. Application Data

[62] Division of Ser. No. 256,933, Apr. 23, 1981, Pat. No. 4,351,843, which is a division of Ser. No. 128,199, Mar. 7, 1980, Pat. No. 4,282,242.

[51] Int. Cl.$^3$ .............................................. A61K 31/40
[52] U.S. Cl. .................................... 514/423; 548/531; 548/532; 548/533; 548/534; 548/536; 514/425; 514/427; 514/866
[58] Field of Search ............... 548/531, 532, 534, 536, 548/533; 424/274

[56] References Cited

U.S. PATENT DOCUMENTS

| | | | |
|---|---|---|---|
| 3,564,016 | 2/1971 | Schoen et al. | 548/531 X |
| 3,752,826 | 8/1973 | Carson | 548/531 X |
| 4,046,775 | 9/1977 | Bailey | 548/532 X |
| 4,048,191 | 9/1977 | Carson | 548/531 X |
| 4,194,003 | 3/1980 | Laforest et al. | 548/536 X |
| 4,282,242 | 8/1981 | Holland | 548/531 X |
| 4,351,843 | 9/1982 | Holland | 548/531 X |

FOREIGN PATENT DOCUMENTS 870910  3/1979  Belgium .

OTHER PUBLICATIONS

Fischer and Orth, "Die Chem. Des. Pyrrols. I, Band", p. 204, (1934).
Bauer et al., J. Med. Chem. 11, pp. 984 to 986, (1968).
Blicke et al., J. Am. Chem. Soc. 66, pp. 1675 to 1677, (1944).
Carson et al., J. Med. Chem. 14, pp. 646 to 647, (1971).
Cheng et al., J. Heterocyclic Chem. 13, pp. 1145 to 1147, (1976).
Corredor et al., Proc. Nat. Acad. Sci. U.S. 58, pp. 2299 to 2306, (1967).
Dulin et al., Proc. Soc. Expt. Biol. Med. 118, pp. 499 to 501, (1965).
Dulin and Gerritsen, Proc. Soc. Expt. Biol. Med. 121, pp. 777 to 779, (1966).
Dulin and Gerritsen, Metab. Clin. Exp. 18, pp. 214 to 225, (1969).
Fringuelli et al., Tetrahedron 25, pp. 5815 to 5818, (1969).
Groves et al., Can. J. Chem. 49, pp. 2427 to 2432, (1971).
Groves et al., Can. J. Chem. 51, pp. 1089 to 1098, (1973).
Kahn et al., Tetrahedron 22, pp. 2095 to 2105, (1966).
Chemical Abstracts 21, 3362.
Lahiri and Pathak, J. Pharm. Sci. 57, pp. 1013 to 1016, (1968).
Sanchez et al., Carb. Res. 3, pp. 486 to 501, (1967).
Smith et al., J. Med. Chem. 8, pp. 350 to 353, (1965).
C.A., 88, 133450k, Chevolot et al.

Primary Examiner—Joseph Paul Brust
Attorney, Agent, or Firm—Connolly and Hutz

[57] ABSTRACT

Certain pyrrolecarboxylic and pyrroleacetic acid derivatives substituted on the pyrrole ring with thioether groups, acyl groups, phenyl, substituted phenyl, phenoxy, substituted phenoxy, benzyl or halo and optionally substituted on the pyrrole nitrogen with alkyl, and the pharmaceutically acceptable salts thereof, are useful in lowering the blood glucose levels of hyperglycemic animals.

5 Claims, No Drawings

ANTIDIABETIC PYRROLECARBOXYLIC ACIDS

CROSS REFERENCE TO RELATED APPLICATIONS

This is a division of application Ser. No. 256,933 filed Apr. 23, 1981, now U.S. Pat. No. 4,351,843 issued Sept. 29, 1982, which in turn is a division of application Ser. No. 128,199 filed Mar. 7, 1980, now U.S. Pat. No. 4,282,242 issued Aug. 4, 1981.

BACKGROUND OF THE INVENTION

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in a high percentage of diabetics where available synthetic hypoglycemic agents are not effective, requires multiple daily, usually self, injection. Determination of the proper dosage of insulin requires frequent estimations of the sugar in the urine or in the blood. The administration of an excessive dose of insulin causes hypoglycemia, with effects ranging from mild abnormalities in blood glucose to coma, or even death. Where effective, synthetic hypoglycemic agents are preferred over insulin, being more convenient to administer and less prone to cause severe hypoglycemic reactions. However, the clinically available hypoglycemics are fraught with other toxic manifestations which limit their use. In any event, where one of these agents may fail in an individual case, another may succeed. The need for additional hypoglycemic agents, which may be less toxic or succeed where others fail, is clearly evident.

In addition to the hypoglycemic agents cited above, a variety of other compounds have been reported to possess this type of activity, including 5-methylpyrazole-3-carboxylic acid [Smith, et al., J. Med. Chem. 8, 350 (1965)], 3-methylisoxazole-5-carboxylic acid [Dulin and Gerritsen, Proc. Soc. Expt. Biol. Med. 121, 777 (1966)], 1-methyl-4-(5-methyl-3-pyrazolyl)pyridinium iodide [Dulin et al., Proc. Soc. Expt. Biol. Med. 118, 499 (1965)], 1-methyl-4-(3-methyl-5-isoxazolyl)pyridinium chloride [Bauer et al., J. Med. Chem. 11, 984 (1968)], 2-carboxypyrazine [Dulin and Gerritsen, Metab. Clin. Exp. 18, 214 (1969)], a series of hexahydroindeno(1,2-c)pyrroles and dialkylaminomethylindans [Lahiri and Pathak, J. Pharm. Sci. 57, 1013 (1968)], methylenecyclopropylacetic acid and 4-pentenoic acid [Corredor et al., Proc. Nat. Acad. Sci. U.S. 58, 2299 (1967)].

A few of the compounds of the present invention have been previously disclosed. 4-Chloropyrrole-2-carboxylic acid, a compound of no known prior utility, has been described by Fringuelli et al. [Tetrahedron 25, 5815 (1969)]. The benzoyl (and substituted benzoyl) pyrrole carboxylic acids (IV, V, VI) of the present invention are generally disclosed by Belgian Pat. No. 870,910 as having uricosuric activity and thus useful in the treatment of gout and related pathological conditions. Certain compounds isomeric to those of the present invention have also been disclosed: 5-chloropyrrole-2-carboxylic acid [Fringuelli et al., loc. cit.; no known utility], 4-benzoylpyrrole-2-carboxylic acid [Groves et al., Can. J. Chem. 49, 2427 (1971); Sanchez et al., Carb. Res. 3, 486 (1967); generally disclosed to have uricosuric activity by Belgian Pat. No. 870,910; not active as hypoglycemic agents in the present case], 3-benzoylpyrrole-2-carboxylic acid [Kahn et al., Tetrahedron 22, 2095 (1966); generally disclosed to have uricosuric activity by Belgian Pat. No. 870,910], 5-phenylpyrrole-2-carboxylic acid [Blicke et al., J. Am. Chem. Soc. 66, 1675 (1944); no known utility] and 2-phenylpyrrole-3-carboxylic acid [Kondo and Suzuki, J. Pharm. Soc. Japan No. 544, 501 (1927); Chem. Abstr. 21, 3362; no known utility].

In some cases, methyl or ethyl esters or other homologs of the compounds of the present invention are known: methyl 4-benzoylpyrrole-3-carboxylate [Groves et al., Can. J. Chem. 51, 1089 (1973); no known utility], methyl 4-chloropyrrole-2-carboxylate [Fringuelli et al., loc. cit.; no known utility], and 5-benzoyl-1-methylpyrrole-2-acetic acids [including tolmetin, the p-methylbenzoyl analog; Carson et al., J. Med. Chem. 14, 646 (1971); which compounds are reported to have anti-inflammatory activity].

SUMMARY OF THE INVENTION

It has now been found that compounds selected from the group consisting of:

(a) a first subgroup consisting of thioethers of pyrrole carboxylic acids of structure I, II or III:

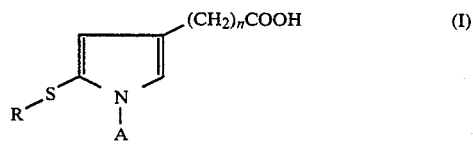

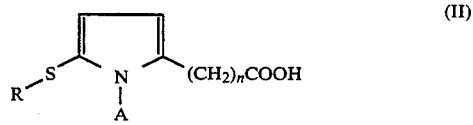

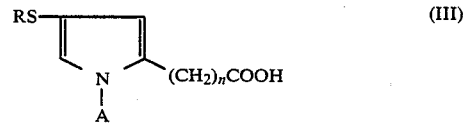

wherein n is an integer of value 0 or 1, A is selected from the group consisting of hydrogen and $(C_1-C_2)$alkyl and R is selected from the group consisting of $(C_1-C_5)$alkyl; benzyl; phenyl; phenyl monosubstituted in the 2-, 3- or 4-position with methyl, methoxy, chloro, fluoro or trifluoromethyl; 2,5-, 2,4- or 3,4-dichlorophenyl; and 2,4,5-trichlorophenyl;

(b) a second subgroup consisting of acylated pyrrole carboxylic acids of structure IV, V or VI:

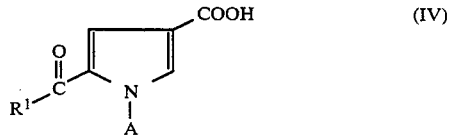

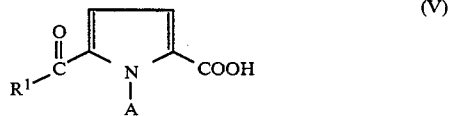

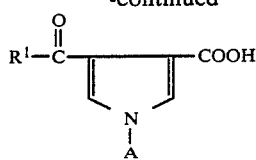

(VI)

wherein A is selected from the group consisting of hydrogen and $(C_1-C_2)$alkyl and $R^1$ is selected from the group consisting of benzyl; cyclohexyl; phenyl; phenyl monosubstituted in the 2-, 3-, or 4-position with methyl, phenyl or chloro; 2,5-dichlorophenyl; and 3,5-dimethoxyphenyl;

(c) a third subgroup consisting of monosubstituted pyrrole carboxylic acids of structure VIII or IX:

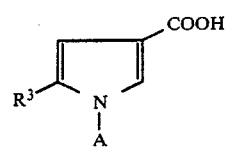

(VIII)

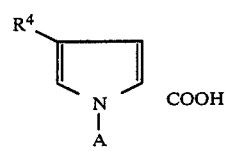

(IX)

wherein A is selected from the group consisting of hydrogen and $(C_1-C_2)$alkyl; $R^4$ is selected from the group consisting of benzyl, phenyl, chloro, 4-chlorophenyl and 4-chlorophenoxy; and $R^3$ is selected from the group consisting of benzyl and chloro;

(d) a fourth group of disubstituted pyrrole carboxylic acids selected from the group consisting of:
4,5-bis(4-methoxyphenylthio)pyrrole-3-carboxylic acid;
1-methyl-4,5-bis(phenylthio)pyrrole-2-carboxylic acid;
4-methyl-5-benzoylpyrrole-3-carboxylic acid;
4-phenyl-5-benzoylpyrrole-3-carboxylic acid;
4-bromo-5-benzoylpyrrole-2-carboxylic acid;
5-bromo-4-benzoylpyrrole-2-carboxylic acid; and
1-methyl-4,5-dibromopyrrole-2-carboxylic acid;
and the pharmaceutically-acceptable cationic salts thereof, when administered in appropriate amount, orally or parenterally, to rodents will lower the level of blood glucose, projecting clinical use of these compounds to reduce the blood levels of glucose in hyperglycemic mammals, including man, to acceptable levels.

By the term "pharmaceutically-acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as benzathine (N,N'-dibenzylethylenediamine), choline, diethanolamine, ethylenediamine, meglumine (N-methylglucamine), benethamine (N-benzylphenethylamine), diethylamine, piperazine and tromethamine (2-amino-2-hydroxymethyl-1,3-propanediol).

Because they possess a high level of activity, compounds of special value in this invention are those of structure I wherein n is O, A is hydrogen, and R is n-butyl, phenyl, 2-, 3- or 4-chlorophenyl, 2,5- or 3,4-dichlorophenyl, 2,4,5-trichlorophenyl or 4-fluorophenyl; that of structure I wherein n is 1, A is hydrogen and R is phenyl; those of structure III wherein n is O, A is hydrogen and R is phenyl or 4-chlorophenyl; those of structure IV wherein A is hydrogen and $R^1$ is cyclohexyl, phenyl, 4-chlorophenyl or 4-phenylphenyl; that of structure IV wherein A is methyl and $R^1$ is phenyl; those of structure V wherein A is hydrogen or methyl and $R^1$ is phenyl; those of structure VIII wherein A is hydrogen and $R^3$ is benzyl or chloro; those of structure IX wherein A is hydrogen and $R^4$ is phenyl, 4-chlorophenyl, 4-chlorophenoxy or chloro, and 1-methyl-4,5-bis(phenylthio)pyrrole-2-carboxylic acid. Because they possess an exceptionally high level of activity, compounds of greatest value in this invention are those of structure I wherein n is O, A is hydrogen and R is n-butyl, phenyl, 2- or 3-chlorophenyl, 2,5- or 3,4-dichlorophenyl, 2,4,5-trichlorophenyl or 4-fluorophenyl; those of structure IV wherein A is methyl and $R^1$ is phenyl or A is hydrogen and $R^1$ is 4-phenylphenyl; that of structure VIII wherein A is hydrogen and $R^3$ is chloro and those of structure IX wherein A is hydrogen and $R^4$ is 4-chlorophenyl or 4-chlorophenoxy.

DETAILED DESCRIPTION OF THE INVENTION

The pyrrolecarboxylic acids of the present invention are prepared using a variety of synthetic methods, depending on the substituent and the position of the substituent desired.

The thioethers of structure I (A=H; n=O) are generally prepared by reaction of a lower alkyl pyrrole-3-carboxylate ester with the appropriate sulfenyl chloride (sulfenylation) followed by acid or base catalyzed hydrolysis of the resulting ester. The sulfenylation is a Friedel-Crafts type reaction. The sulfenyl halides, being highly reactive, do not require the addition of a catalyst, although the reaction is self-catalyzed by the hydrogen chloride produced in the reaction. The reaction is conveniently carried out by mixing the reagents in an inert solvent such as an aromatic hydrocarbon (e.g. benzene, toluene), a halogenated aromatic or aliphatic hydrocarbon (e.g. chlorobenzene, methylene chloride, ethylene chloride, chloroform), or an ether (tetrahydrofuran, 1,2-dimethoxyethane). As a matter of safety, since this reaction is in some cases exothermic, the sulfenyl chloride, as a solution or neat, is conveniently added dropwise to a solution of the furan-2-carboxylate at reduced temperature. The reaction is then allowed to proceed at room temperature until substantially complete (about 1-16 hours). Temperature is not critical, and can be substantially above or below ambient (e.g. 0°-50° C.); at lower temperatures, the reaction time is extended beyond the 16 hour range if necessary. At the higher part of the temperature range, shorter reaction times (e.g. 15 minutes to 2 hours) are employed. The thioether esters are isolated by evaporation of solvent, followed by standard recrystallization or chromatographic procedures. If desired, crude ester can be hydrolyzed, leaving purification to the final stage of the synthesis. Hydrolysis of the resulting esters is readily carried out under a variety of conditions, employing acid or base catalysis, well known in the chemical art. Conveniently, the hydrolysis is carried out in a mixture of aqueous sodium hydroxide and either methanol or ethanol, by heating for 1-4 hours on a steam bath under reflux or in an open flask. Product is isolated by evaporation of any remaining alcohol, acidification, and filtration or extraction into an organic solvent such as ethyl acetate and evaporation to dryness. Further purification, when desired, is by standard recrystallization or chromatographic techniques.

When thioethers of the structure I (A=CH$_3$ or C$_2$H$_5$; n=O) are desired, it is convenient to alkylate the intermediate esters, prior to hydrolysis as described immediately above. Methylation or ethylation is conveniently carried out by first converting the 5-substituted-pyrrole-2-carboxylate ester to the sodium salt by reaction with sodium hydride in an inert solvent (i.e. one which will not itself react with sodium hydride, e.g. tetrahydrofuran, dimethoxyethane, benzene), followed by reaction with an alkylating agent (e.g., dimethylsulfate, methyl iodide, methyl bromide, ethyl iodide, ethyl chloride, etc.). Formation of the sodium salt is generally carried out at room temperature in the presence of excess sodium hydride for 1 hour, more or less. Subsequent alkylation is carried out, usually in the same solvent, by addition of excess alkylating agent and reaction at 0°-50° C. for 1 to 24 hours, conveniently ambient temperature for about 16 hours.

The sulfenyl chlorides required as starting materials are readily available by the reaction of the appropriate mercaptan with N-chlorosuccinimide or chlorine in an inert solvent (carbon tetrachloride, chloroform, methylene chloride, benzene, tetrahydrofuran, 1,2-dimethoxyethane, etc.) at 0°-50° C. until reaction is substantially complete (2-48 hours)—conveniently at ambient temperature for about 16 hours. Methyl or other lower alkyl pyrrole-3-carboxylates are conveniently prepared by the condensation of tosylmethyl isocyanide with methyl or other alkyl acrylate, in a solvent such as tetrahydrofuran with sodium hydride as the source of basic catalyst.

The thioethers of structure II (n=O, A=H) are generally prepared by sulfenylation of pyrrole (under conditions described above for the sulfenylation of alkyl pyrrole-3-carboxylates, yielding in this case 2-sulfenylpyrroles) followed by trichloroacetylation at the other alpha position (Friedel-Crafts conditions similar to the initial sulfenylation) to yield intermediate 5-sulfenyl-2-trichloroacetyl derivatives, and finally hydrolysis (conditions identical with those described above for ester hydrolyses) to yield the desired 5-sulfenylpyrrole-2-carboxylic acids. When 1-methyl or ethyl derivatives (II, n=O, A=CH$_3$ or C$_2$H$_5$) are desired, they can be obtained by dialkylation of the acids (II, n=O, A=H) under the alkylation conditions described above, followed by hydrolysis of the resulting ester, again as described above.

The thioethers of structure III (n=O, A=H) are generally prepared by the sulfenylation of pyrrole-2-carboxylic acid. Conditions are like the sulfenylation conditions described above, except that a reaction period up to five times longer is employed. The now acidic products are conveniently isolated by replacement of the solvent with a water-immiscible solvent (if necessary), extraction of the product into sodium hydroxide, acidification, filtration or extraction into an organic solvent such as ethyl acetate and evaporation to dryness. If necessary, the product is purified by standard recrystallization techniques or chromatography. When the 1-alkyl derivatives encompassed by structure II are desired, they are prepared from the acids by the methods described in the paragraphs above.

When compounds of the structures I, II, or III, wherein n=1, are desired, they can be prepared by sequential hydride reduction of the appropriate acid or ester, to pyrrolylmethyl alcohols, conversion of the alcohol to the corresponding tosylate, mesylate, etc. and then to the nitrile. Hydrolysis of the nitriles produces the desired acids. The hydride reductions can be carried out with a variety of reagents, generally under mild conditions. The most common commercially available hydride reducing agents are diborane, lithium aluminum hydride, lithium borohydride, and sodium borohydride. The latter can be activated by addition of lithium chloride or aluminum chloride. Also commercially available is a less reactive derivative of lithium aluminum hydride sold under the tradename "Red-al," which is a 70% solution of bis(2-methoxyethoxy)aluminum hydride in benzene, and lithium aluminum hydride as a 50% suspension in oil, which is more readily handled than lithium aluminum hydride itself. The reduction of carboxylic acids and esters requires a strong hydride reducing agent such as diborane, lithium aluminum hydride or sodium borohydride activated with aluminum chloride. It is essential that the solvent for such a hydride reduction be aprotic and free of reducible groups (carbonyl function of any type, nitrile, nitro, aliphatic halogen, sulfonate, etc.). The preferred solvents are ethers such as tetrahydrofuran, dioxane, 1,2-dimethoxyethane, bis(2-methoxyethyl)ether , etc. Temperature and reaction time are not critical, usually being in the range 0°-100° C. for up to 24 hours. For reduction of esters the same reagents as those employed for reduction of acids can be employed. Lithium borohydride alone can also be employed, but more vigorous conditions (e.g. refluxing tetrahydrofuran) are required. Also well-suited for the reduction of esters is Red-al (discussed above). Suitable solvents for use with Red-al are toluene, benzene, diethylether, tetrahydrofuran, dimethoxyethane, etc. Temperature and reaction times are as discussed immediately above. The intermediate tosylates, mesylates, etc., are readily obtained by reaction of tosyl chloride, mesyl chloride, etc. with the alcohol in an inert solvent (such as those defined above for sulfenylations) over a wide temperature range (e.g. −50° to 80° C.) in the presence of a basic catalyst, preferrably a tertiary amine such as triethylamine. The reaction is rapid, being complete in a matter of minutes at room temperature. As an alternative, the alcohols can be reacted with reagents such as dry halogen halide, or phosphorous halides to yield the corresponding halide, which can be substituted for the tosylate, mesylate, etc., in the next step. The tosylate, mesylate, etc., can be isolated by standard methods, or used directly in the next step without isolation. Replacement of mesylate (or other group) is effected by cyanide anion, usually in the form of the potassium or sodium salt. A wide variety of solvents are suitable for this reaction, including water, alcohols, ketones, ethers, halogenated hydrocarbons, acetonitrile, dimethylformamide, etc., or miscible combinations thereof. The only requirements are that the solvent be inert towards reactants and product, that the reactants have some degree of solubility, and that the solvent be less acidic than hydrogen cyanide so as to maintain the anionic form thereof. The temperature employed for this reaction is not critical (e.g. 0°-120° C.). It should be high enough to provide a reasonable rate, but not so high as to lead to undue decomposition. As is well known in the art, rate will vary with the nature of the group displaced, the structure of the substrate, the solvent, the temperature and the concentration of the reactants. To maximize yields, the reaction time should be such that the reaction is nearly complete (e.g. >95% conversion when equivalent amounts of mesylate and cyanide are employed). These reactions are readily monitored by thin layer chromatography, employing one of a variety of commercially available silica gel plates containing an ultraviolet indicator. Suitable eluants are ethyl acetate/hexane/methanol mixtures with about 5% added acetic acid. The proportion of these solvents is varied with the polarity of the reactant and product, a practice well-known in the art. For most of the reactions of this type, an eluant consisting of 5 parts of ethyl acetate and 1 part of hexane together with 5% acetic acid is well suited. For the more polar compounds the proportion of ethyl acetate is increased (e.g. 1 ethyl acetate, 1 hexane). The final step, hydrolysis of nitrile to acid, is carried out under conditions identical to those described above for the hydrolysis of alkyl esters.

In the case of compounds of the structure I, II and III, wherein n=1 and A=CH₃ or C₂H₅, they can also be prepared by alkylation of the acids of structure I, II or III, wherein n=1 and A=H, and hydrolysis of the resulting ester, using methods described above. Alkylation can also be carried out at various precursor stages, e.g. on alcohol or nitrile.

Thioethers of the structure II (n=1, C=CH₃ or C₂H₅) are alternatively prepared by sulfenylation of 1-alkyl-2-pyrrolylacetonitrile, followed by hydrolysis, both reactions being carried out as described above. Further variation in the sequence of steps for preparing compounds I, II and III (A=CH₃ or C₂H₅) will be evident to those skilled in the art.

5-Acylpyrrole-3-carboxylic acids of structure IV, wherein A=H are prepared by Friedel-Crafts type acylation of a lower alkylpyrrole-3-carboxylate, followed by hydrolysis of the resulting ester. The acylation is generally carried out using an acid halide, usually the acid chloride, as the acylating agent. The acylation conditions (solvent, temperature, time) are identical to those described above for sulfenylations, except that an added Lewis acid catalyst is generally employed. A convenient catalyst is stannic chloride, but a wide variety of other catalysts (e.g. aluminum chloride) are also useful for this purpose.

Acid halides required in the above syntheses, when not available commercially, are readily available by standard methods from the corresponding acids, e.g. reaction of thienyl chloride with acids in methylene chloride (optionally with a trace of dimethylformamide as catalyst) is but one of many convenient ways of preparing acid chlorides from carboxylic acids.

Alternatively, 5-acylpyrrole-3-carboxylic acids are prepared from alpha-haloketones, employing the following route:

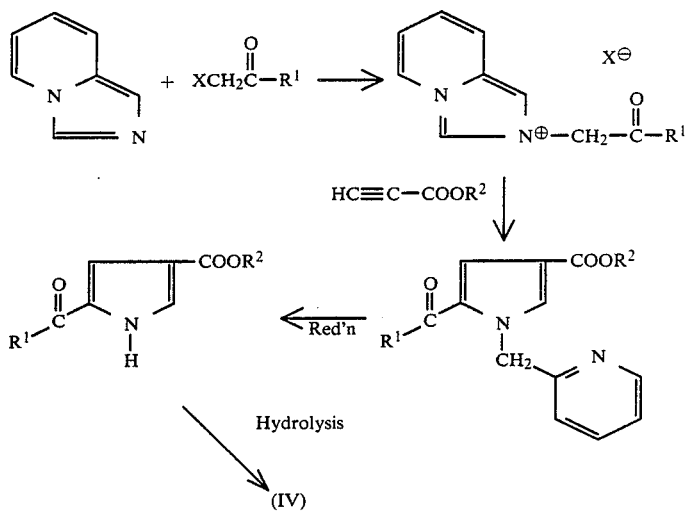

The initial reaction of alpha-haloketone with imidazo[3,4-a]pyridine is carried out under conditions identical to those described above for the reaction of cyanide with mesylate esters, in this case the solvent being sufficiently non-acidic that the amine group is not protonated. Since the reactants/products are relatively polar, a relatively polar thin layer chromatographic system is used to monitor this reaction—e.g. ethyl acetate/5% acetic acid as eluant. Condensation of the resulting salt with a lower alkyl propiolate (e.g. R²=CH₃ or C₂H₅) affords the lower alkyl 1-(2-pyridylmethyl)-5-acylpyrrole-3-carboxylate. The latter reaction is facile in the presence of a weak base catalyst, such as potassium carbonate, in a polar, aprotic solvent such as dimethylformamide. The reaction is carried out at a temperature between −10° C. and 50° C., conveniently ambient temperature, from 30 minutes to up to several days, depending upon the temperature selected. The reaction is conveniently monitored by thin layer chromatography, as in the preceding step. The 1-(2-pyridylmethyl) group is removed by reductive means (e.g. selenium dioxide in wet dioxane at 60°–120° C., for 4–60 hours depending upon temperature; temperatures above the boiling point of dioxane are achieved by running the reaction under pressure). Finally, the ester is hydrolyzed by methods described above to yield the desired acid.

The imidazo[3,4-a]pyridine required for the above syntheses is readily prepared by formylation of 2-aminomethylpyridine followed by cyclization in the presence of excess phosphorus oxychloride. The necessary alpha-haloketones are available commercially, in the literature or by literature methods.

1-Alkyl derivatives of the structure IV (A=CH₃ or C₂H₅) are prepared from the corresponding esters via the two step alkylation-hydrolysis procedures described above.

5-Acylpyrrole-2-carboxylic acids (V, A=H) are prepared by two stage Friedel-Crafts acylation of alkyl pyrrole-2-carboxylates and hydrolysis, both reactions carried out according to procedures described above. The corresponding 1-alkyl derivatives (V, A=CH$_3$ or C$_2$H$_5$) are prepared from the intermediate esters via the alkylation-hydrolysis procedure also described above.

5-Chloropyrrole-3-carboxylic acid (VIII, R$^3$=Cl, A=H) is prepared by chlorination of lower alkyl pyrrole-3-carboxylate and hydrolysis of the resulting ester. When the corresponding 1-alkyl derivatives (VIII, R$^3$=Cl, A=CH$_3$ or C$_2$H$_5$) are desired, the intermediate esters are alkylated prior to hydrolyses. Chlorination is conveniently carried out with excess tert.-butyl hypochlorite as reagent in a solvent such as methylene chloride. Alkylations and hydrolyses are carried out as described above.

5-Benzylpyrrole-3-carboxylic acid (VIII, R$^3$=C$_6$H$_5$CH$_2$, A=H) and 1-alkyl-5-benzylpyrrole-3-carboxylic acids (VIII, R$^3$=C$_6$H$_5$CH$_2$, A=CH$_3$ or C$_2$H$_5$) are conveniently prepared by reduction of the corresponding 5-benzoylpyrrole-3-carboxylic acids (IV, R$^1$=C$_6$H$_5$). The use of excess hydrazine and potassium hydroxide at elevated temperature (e.g. 100°-150° C.) in a solvent such as ethylene glycol are conditions well-suited for this purpose. The corresponding 4-benzylpyrrole-2-carboxylic acid (IX, R$^4$=C$_6$H$_5$CH$_2$, A=H) is prepared in the same manner from known 4-benzoylpyrrole-2-carboxylic acid. 1-Alkyl derivatives of IX are prepared by methods described above.

The compounds of structure IX wherein R$^4$ is 4-chlorophenoxy or 4-chlorophenyl are prepared by the following route:

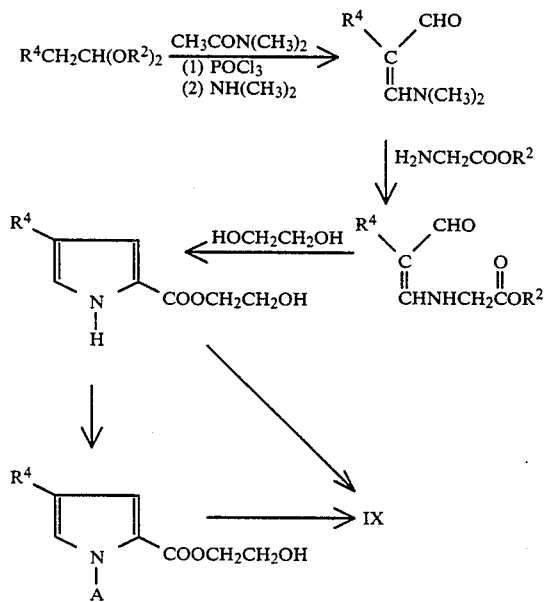

The appropriately substituted acetaldehyde di(lower alkyl)acetal (e.g. R$^2$=CH$_3$ or C$_2$H$_5$) is reacted with dimethylformamide and phosphorous oxychloride and then with dimethylamine to yield the intermediate 3-dimethylamino acrylaldehyde, which in turn is reacted with a lower alkyl glycinate (e.g. R$^2$=CH$_3$ or C$_2$H$_5$) to yield the pyrrole precursor. The cyclization is carried out by simple heating of the starting material in ethylene glycol. The lower alkyl ester (e.g. R$^2$=CH$_3$ or C$_2$H$_5$) is simultaneously converted to the glycol ester. Alkylations and hydrolyses are carried out as described above. Compounds of the structure IX wherein R$^4$ is phenyl or benzyl can also be obtained by substitution of the appropriate acetal as starting material. Alternative synthesis of the benzyl compounds are described above. Alternative synthesis of the phenyl compounds is by hydrogenolysis of the corresponding 4-chlorophenyl derivatives (e.g. hydrogenation over palladium-on-carbon in ethanol/triethylamine).

The disubstitutedpyrrole carboxylic acids of this invention are prepared according to the methods detailed in the specific examples provided below.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness, or by addition of a non-solvent. In some cases, salts can be prepared by mixing a solution of the acid with a solution of a different salt of the cation (e.g. sodium ethylhexanoate, magnesium oleate), employing a solvent in which the desired cationic salt precipitates, or can be otherwise isolated by concentration and/or addition of a non-solvent.

The pyrrolecarboxylic acids of the present invention are readily adapted to clinical use as antidiabetic agents. The hypoglycemic activity required for this clinical use is well illustrated by the test procedure which follows.

Intact male albino rats, each weighing approximately 200 grams are the experimental test animals employed for such purposes. The test animals are fasted approximately 18-24 hours. The rats are weighed, numbered, and recorded in groups of five or six as needed. Each animal is then dosed with glucose (usually one gram per kilogram) intra-peritoneally, and then either saline (controls) or compound. The treated animals are given the pyrrolecarboxylic acid to be tested at a dosage of 100 mg./kg. or less; in each instance, the drug is suspended or dissolved in an aqueous system, and the doses are administered orally or parenterally. Blood glucose is measured over a period of 3 house in both control and treated groups. The results obtained are expressed in terms of the percentage decrease in the blood glucose value of treated animals from the control value. Those compounds which decrease the blood glucose by 20% or better are considered to have high activity; while those which decrease it by 30% or better are considered to have exceptionally high activity. In this connection, it is significant to note that the results obtained show that the compounds of the present invention exhibit a hypoglycemic effect which is comparable to that afforded by known clinically useful anti-diabetics in this field.

The pyrrolecarboxylic acids of the present invention are clinically administered to diabetic mammals, including man, via either the oral or the perenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg./kg.

body weight of the subject per day, preferably about 0.10 to about 10 mg./kg. body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmceutical preparations containing the compound, or a pharmaceutically-acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amount sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like may be used, as well as aqueous solutions of water-soluble pharmaceutically-acceptable salts of the compounds. The injectable solutions prepared in this manner can then be administered intravenously, intraperitoneally, subcutaneously or intramuscularly, with intramuscular administration being preferred in man.

The present invention is illustrated by the following examples. However, it should be understood that the invention is not limited to the specific details of these examples.

EXAMPLE 1

Methyl Pyrrole-3-Carboxylate

Sodium hydride (57% dispersion in oil, 10.5 g., 0.25 mole) was placed in a flame dried flask and washed twice with dry benzene. Dry tetrahydrofuran (400 ml.) was added to the flask and the resulting slurry stirred under nitrogen. A mixture of methyl acrylate (11.3 ml., 0.128 moles) and tosylmethyl isocyanide (25 g., 0.128 moles) in 120 ml. of tetrahydrofuran was then added dropwise over 30 minutes. The reaction was exothermic and the reaction mixture refluxed during this process. After stirring for an additional hour (without external heating), the reaction mixture was cooled in an ice-water bath and water (approx. 120 ml.) added dropwise until solution resulted. The solution was allowed to warm and then extracted three times with ether. The combined ether extracts were back-washed with water and then saturated brine, dried over anhydrous sodium sulfate, filtered and evaporated in vacuo to yield methyl pyrrole-3-carboxylate (6.4 g., m.p. 78°–81° C., m/e 125).

Substitution of ethyl, propyl, isopropyl, phenyl, or benzyl acrylate for methyl acrylate is used to produce the corresponding ethyl, propyl, isopropyl, phenyl, or benzyl pyrrole-3-carboxylates.

EXAMPLE 2

Benzenesulfenyl Chloride

Under a nitrogen atmosphere, N-chlorosuccinimide (16.3 g., 0.22 mole) was slurried in 125 ml. of methylene chloride. While stirring at room temperature, benzenethiol (13.2 g., 0.12 mole) was added; 2 ml. initial addition to start reflux and the remainder at a rate to maintain reflux (approx. 10 min.). The clear solution which resulted was then stirred at room temperature for 30 minutes. A small amount of precipitate which formed was removed by filtration. The filtrate, assumed to contain the theoretical quantity of benzenesulfenyl chloride (17.3 g., 0.12 mole), was used immediately and directly in the next step. Alternatively, benzenesulfenyl chloride was isolated by evaporation to an oil prior to its further use.

EXAMPLE 3

Methyl 5-phenylthiopyrrole-3-carboxylate

Methyl pyrrole-3-carboxylate (15 g., 0.12 mole) was dissolved in 200 ml. of methylene chloride under nitrogen and cooled in an ice-water bath. Benzenesulfenyl chloride (approx 17.3 g., 0.12 moles) in approximately 125 ml. of methylene chloride (freshly prepared by the procedure of Example 2) was added dropwise over to the stirred reaction mixture. The ice-water bath was removed and the reaction stirred for 1 hour at room temperature. A volume of ether equal to that of the reaction mixture was added and the mixture clarified by filtration. The filtrate was washed with water and saturated brine, dried over anhydrous sodium sulfate, filtered and evaporated to an oil (26 g.). The oil was chromatographed on 300 g. of silica gel with ethyl acetate/hexane (7/1) as eluant. Fractions of 200 ml. volume were collected. Fractions 3 to 8 were evaporated to yield methyl 5-phenylthiopyrrole-3-carboxylate (6.9 g., m.p. 107°–109° C.)

The same procedure is employed to convert ethyl, propyl, isopropyl, phenyl or benzyl pyrrole 3-carboxylates to, respectively:
Ethyl 5-phenylthiopyrrole-3-carboxylate;
Propyl 5-phenylthiopyrrole-3-carboxylate;
Isopropyl 5-phenylthiopyrrole-3-carboxylate;
Phenyl 5-phenylthiopyrrole-3-carboxylate; and
Benzyl 5-phenylthiopyrrole-3-carboxylate.

EXAMPLE 4

5-Phenylthiopyrrole-3-carboxylic Acid

Methyl 5-phenylthiopyrrole-3-carboxylate (6.8 g.) was combined with 70 ml. of 1N sodium hydroxide and 120 ml. of methanol and heated to reflux for 3 hours. Methanol was evaporated, an equal volume of water added and impurities extracted into ether. The aqueous phase was acidified with conc. hydrochloric acid, and precipitated 5-phenylthiopyrrole-3-carboxylic acid (6.1 g., m.p. 145°–147° C., m/e 219) recovered by filtration.

By the same procedure ethyl, propyl, isopropyl, phenyl and benzyl 5-phenylthiopyrrole-3-carboxylates are converted to 5-phenylthiopyrrole-3-carboxylic acid.

EXAMPLE 5

Methyl 1-Methyl-5-phenylthiopyrrole-3-carboxylate 5-phenylthiopyrrole-3-carboxylic acid (470 mg., 2 mmoles) was combined with sodium hydride (170 mg. of 57% in oil dispersion, 4 mmoles) and 50 ml. of ether and stirred under nitrogen for 1 hour at room temperature. To the sodium salt thus formed, was added dimethylsulfate (0.4 ml., 4.2 mmoles) and the reaction stirred for approximately 16 hours. Thin layer chromatography on silica gel with ethyl acetate-1/hexane-5/5% acetic acid indicated the reaction was complete. The reaction mixture was concentrated to dryness to yield methyl 1-methyl-5-phenylthiopyrrole-3-carboxylate (sodium salt) used directly in the next step.

The same product is also prepared by substituting an equivalent of methyl iodide for dimethylsulfate in an otherwise identical process. Substitution of an equivalent of ethyl iodide, in this process will produce ethyl 1-ethyl-5-phenylthiopyrrole-3-carboxylate.

The same procedures are used to prepare 1-alkylpyrroles and alkyl 1-alkylpyrrolecarboxylates from pyrrole and alkyl pyrrolecarboxylates, respectively, except that only one equivalent of sodium hydride and one equivalent of the alkylating agent is employed.

EXAMPLE 6

1-Methyl-5-phenylthiopyrrole-3-carboxylic Acid

The entire crude methyl 1-methyl-5-phenylthiopyrrole-3-carboxylate from Example 5 was taken up in 30 ml. of methanol and 15 ml. of 1N sodium hydroxide and boiled for 2 hours. The aqueous residue was extracted with ether to remove impurities and then acidified to precipitate 1-methyl-5-phenylthiopyrrole-3-carboxylic acid (427 mg., m.p. 160°-162° C., m/e 233).

Analysis: Calcd. for $C_{12}H_{11}O_2N_2S$: C, 61.80; H, 4.75; N, 6.01. Found: C, 62.17; H, 4.73; N, 6.05.

By the same process the corresponding 1-ethyl derivative of Example 5 is converted to 1-ethyl-5-phenylthiopyrrole-3-carboxylic acid.

EXAMPLE 7 o-Toluenesulfenyl Chloride

N-chlorosuccinimide (5.34 g., 40 mmoles) was slurried in 50 ml. of benzene and cooled in an ice-water bath. o-Toluenethiol (4.96 g., 40 mmoles) in 50 ml. of benzene was added dropwise over 15 minutes. The reaction was warmed to room temperature and stirred for approximately 16 hours. The reaction mixture was filtered and o-toluenesulfenyl chloride (5.53 g.) obtained as an oil by evaporation in vacuo.

EXAMPLE 8

Methyl 5-(2-Methylphenylthio)pyrrole-3-carboxylate

Under a nitrogen atmosphere, methyl pyrrole-3-carboxylate (2.5 g., 20 mmoles) was dissolved in 50 ml. of methylene chloride. The stirred solution was cooled in an ice-water bath and o-toluenesulfenyl chloride (3.16 g., 20 mmoles) was added dropwise. The reaction mixture was warmed to room temperature and stirred for 1 hour. Thin layer chromatography (silica gel, chloroform eluant) indicated virtually complete reaction at this time. An equal volume of ether was added and a small amount of insolubles removed by filtration. Crude product (5 g.) was obtained by evaporation in vacuo to a gum. The latter was chromatographed on 150 g. of silica gel with 75 ml. fractions of the chloroform eluant collected. Fractions 10 to 13 were combined and evaporated in vacuo to yield partially purified product (1.69 g., m.p. 114°-119° C.). Recrystallization from methylene chloride/hexane gave purified methyl 5-(2-methylphenylthio)pyrrole-3-carboxylate (1.1 g., m.p. 126°-128° C.).

EXAMPLE 9

5-(2-Methylphenylthio)pyrrole-3-carboxylic Acid

Methyl 5-(2-methylphenylthio)pyrrole-3-carboxylate (1.1 g.) was combined with 20 ml. of 1N sodium hydroxide and 50 ml. of methanol and refluxed for 2.5 hours, at which time thin layer chromatography with hexane-5/ethyl acetate-1/5% acetic acid as eluant indicated reaction to be complete. Methanol was removed by evaporation, the aqueous residue was diluted with approximately one volume of water, and extracted with ether. The aqueous phase was acidified with 6N hydrochloric acid and the product extracted into ethyl acetate. The ethyl acetate was washed with saturated brine, dried over anhydrous sodium sulfate, filtered, and concentrated in vacuo to crude product (1.0 g.). Recrystallization from methylene chloride/hexane gave purified 5-(2-methylphenylthio)pyrrole-3-carboxylic acid (590 mg., m.p. 151°-153° C., m/e 233).

Analysis: Calcd. for $C_{12}H_{11}O_2NS$: C, 61.77; H, 4.75; N, 6.0. Found: C, 62.04; H, 4.75; N, 5.87.

EXAMPLE 10 p-Toluenesulfenyl Chloride

By the method of Example 7, 6.2 g. of p-toluenethiol (6.2 g., 50 mmoles) was reacted with N-chlorosuccinimide (6.67 g., 50 mmoles) in 100 ml. of benzene to yield p-toluenesulfenyl chloride (7.0 g.) as an oil.

By the same method m-toluenethiol [Tarbell and Fukushima, Org. Synthesis 27, 81 (1947)] is converted to m-toluenesulfenyl chloride.

EXAMPLE 11

Methyl 5-(4-methylphenylthio)pyrrole-3-carboxylate

Methyl pyrrole-3-carboxylate (2.5 g., 20 mmoles) was dissolved in 50 ml. of methylene chloride. To the stirred solution there was added dropwise p-toluenesulfenyl chloride (2.92 g., 20 mmoles), with the temperature maintained below 30° C. by occasional cooling with an ice-water bath. The reaction was stirred for 60 minutes at room temperature. The reaction mixture was concentrated in vacuo to an oil. The residue was taken up in a mixture of isopropyl alcohol and hexane, a small amount of gum removed by filtration and the filtrate reevaporated in vacuo to an oil (5.0 g.). The latter was chromatographed on 150 g. of silica gel, with 100 ml. fractions of the benzene eluant collected. Fractions 10 to 19 were combined to yield the desired product (1.41 g.) contaminated with an impurity showing a mass spectral peak at 281. The latter was removed by recrystallization from methylene chloride/hexane to yield purified methyl 5-(4-methylphenylthio)pyrrole-3-carboxylate (1.14 g., m.p. 118°-121° C., m/e 247).

By the method of this Example and Examples 3 and 8, methyl pyrrole-3-carboxylate is reacted with m-toluenesulfenyl chloride to yield methyl 5-(3-methylphenylthio)-pyrrole-3-carboxylate.

EXAMPLE 12

5-(4-Methylphenylthio)pyrrole-3-carboxylic Acid

Methyl 5-(4-methylphenylthio)pyrrole-3-carboxylate (700 mg.) was refluxed with 15 ml. of 1N sodium hydroxide and 30 ml. of methanol for 2.5 hours. The methanol was removed by evaporation and the aqueous residue cooled to room temperature and extracted with ether. The aqueous layer was acidified and the product extracted multiply with ethyl acetate. The ethyl acetate extracts were combined, washed with saturated brine, dried over anhydrous sodium sulfate, filtered, and evaporated to an oil, which crystallized on standing (700 mg.). Recrystallization from methylene chloride/hexane gave purified 5-(4-methylphenylthio)pyrrole-3-carboxylic acid (432 mg., m.p. 155°–157° C., m/e 233).

Analysis: Calcd. for $C_{12}H_{11}O_2NS.0.125\ H_2O$: C, 61.21; H, 4.78; N, 5.95. Found: C, 61.36; H, 4.67; N, 5.46.

By the same procedure the other ester of Example 11 is hydrolyzed to:

5-(3-Methylphenylthio)pyrrole-3-carboxylic acid.

EXAMPLE 13 o-Chlorobenzenesulfenyl Chloride

Under nitrogen, N-chlorosuccinimide (5.34 g., 40 mmoles) was slurried in 50 ml. of carbon tetrachloride and the stirred mixture cooled in an ice-water bath. o-Chlorothiophenol (5.76 g., 40 mmoles), dissolved in 25 ml. of carbon tetrachloride, was added dropwise. The ice-water bath was removed and the reaction mixture stirred at room temperature for approximately 16 hours. The reaction was filtered, evaporated to an oil, taken up in hexane, refiltered and reconcentrated to yield o-chlorobenzenesulfenyl chloride (6.8 g., oil).

EXAMPLE 14

Methyl 2-(2-Chlorophenylthio)pyrrole-3-carboxylate

Under a nitrogen atmosphere, methyl pyrrole-3-carboxylate (2.5 g., 20 mmoles) was dissolved in 50 ml. of methylene chloride and cooled in an ice-water bath. To the stirred solution o-chlorosulfenyl chloride (3.56 g., 20 mmoles) was added dropwise. The ice-water bath was removed and the reaction was stirred at room temperature for 1 hour. An equal volume of ether was added to the reaction mixture, which was filtered and crude product isolated by evaporation of the filtrate to an oil (4.5 g.). The oil was crystallized from methylene chloride and hexane to yield purified methyl 5-(2-chlorophenylthio)pyrrole-3-carboxylate (2.0 g., m.p. 124°–130° C.).

EXAMPLE 15

5-(2-Chlorophenylthio)pyrrole-3-carboxylic Acid

Methyl 5-(2-chlorophenylthio)pyrrole-3-carboxylate (2.0 g.) was combined with 20 ml. of methanol and 20 ml. of 1N sodium hydroxide and refluxed for 2 hours. The methanol was allowed to evaporate and the aqueous residue diluted with approximately one volume of water, acidified with hydrochloric acid and the product extracted multiply into ethyl acetate. The ethyl acetate extracts were combined, washed with saturated brine, dried over anhydrous sodium sulfate, filtered and concentrated in vacuo to a gum. The gum was crystallized by trituration with hexane and crude product (1.0 g., m.p. 160°–166° C.) recovered by filtration. Recrystallization from methylene chloride/hexane gave purified 5-(2-chlorophenylthio)pyrrole-3-carboxylic acid (m.p. 174°–176° C., m/e 253).

Analysis: Calcd for $C_{11}H_8O_2NClS.0.25\ H_2O$ C, 51.06; H, 3.29; N, 5.41. Found: C, 51.09; H, 3.27; N, 5.47.

EXAMPLE 16 m-Chlorobenzenesulfenyl Chloride

By the same method as Example 13, m-chlorothiophenol (5.76 g., 40 mmoles) was converted to m-chlorobenzenesulfenyl chloride (6.09 g. of oil).

EXAMPLE 17

Methyl 5-(3-Chlorophenylthio)pyrrole-3-carboxylate

By the procedure of Example 14, methyl pyrrole-3-carboxylate (2.5 g., 20 mmoles) was reacted with m-chlorobenzenesulfenyl chloride to yield crude product as an oil (5.0 g.). The crude was chromatographed on 250 g. of silica gel, with 100 ml. fractions of the methylene chloride eluant collected. Fractions 17 to 30 were combined and evaporated to yield purified methyl 5-(3-chlorophenylthio)pyrrole-3-carboxylate (1.8 g., m.p. 90°–95° C., m/e 267) which crystallized on standing.

EXAMPLE 18

5-(3-Chlorophenylthio)pyrrole-3-carboxylic Acid

Methyl 5-(3-chlorophenylthio)pyrrole-3-carboxylate (1.5 g.) was refluxed with 10 ml. of 1N sodium hydroxide and 20 ml. of methanol, at which time thin layer chromatography (silica gel with hexane-5/ethyl acetate-1/5% acetic acid as eluant) indicated hydrolysis was complete. The methanol was allowed to evaporate. The aqueous residue was diluted with approximately one volume of water and extracted twice with ether. The aqueous phase was acidified with 6N hydrochloric acid and product extracted multiply into ethyl acetate. The combined ethyl acetate extracts were back-washed with water and then with saturated brine, dried over anhydrous sodium sulfate and evaporated to an oil. Trituration of the oil with hexane gave 5-(3-chlorophenylthio)pyrrole-3-carboxylic acid (1.32 g., m.p. 134°–137° C., m/e 253).

Analysis: Calcd. for $C_{11}H_8O_2NClS$: C, 52.07; H, 3.17; N, 5.52. Found: C, 52.27; H, 3.27; N, 5.52.

EXAMPLE 19 p-Chlorobenzenesulfenyl Chloride

Following the method of Harpp and Mathiaparnam [J. Org. Chem. 37, 1372 (1972)], 14.4 g. of p-chlorothiophenol was converted to 16 g. of p-chlorobenzenesulfenyl chloride (oil).

Alternatively, p-chlorosulfenyl chloride is prepared by the procedure of Example 13.

EXAMPLE 20

Methyl 5-(4-chlorophenylthio)pyrrole-3-carboxylate

Methyl pyrrole-3-carboxylate (2.5 g., 20 mmole) was dissolved in 35 ml. of methylene chloride. p-Chlorobenzenesulfenyl chloride (4.0 g., 22 mmoles) was added dropwise over approximately 2 minutes, and the reaction mixture was stirred at room temperature for 1 hour. Two volumes of ether were added, the mixture extracted twice with 20 ml. portions of water and the organic layer evaporated in vacuo. The resulting oil was chromatographed on 100 g. of silica gel with approximately 25 ml. fractions of the ethyl acetate-1/hexane-7 eluant collected. Fractions 19 to 36 were combined and concentrated to yield methyl 5-(4-chlorophenylthio)pyrrole-3-carboxylate (1.4 g., m.p. 122°–124° C.).

EXAMPLE 21

5-(4-Chlorophenylthio)pyrrole-3-carboxylic Acid

Methyl 5-(4-chlorophenylthio)pyrrole-3-carboxylate (1.4 g.) was combined with 20 ml. of methanol and 20 ml. of 1N sodium hydroxide and heated on a steam bath for 2 hours. The reaction was cooled, acidified with conc. hydrochloric acid. and the crude product which precipitated, collected by filtration. Two recrystallizations from acetone/hexane afforded purified 5-(4-chlorophenylthio)pyrrole-3-carboxylic acid (740 mg., m.p. 171°–173° C.).

Analysis: Calcd for $C_{11}H_8O_2SCl$: C, 52.07; H, 3.18; N, 5.52. Found: C, 52.20; H, 3.17; N, 5.52.

EXAMPLE 22

2,5-Dichlorobenzenesulfenyl Chloride

The procedure of Example 13 was repeated, reacting a slurry of N-chlorosuccinimide (3.72 g., 27.9 mmoles) in 50 ml. of carbon tetrachloride with 2,5-dichlorothiophenol (5.0 g., 27.9 mmoles) in 25 ml. of carbon tetrachloride. 2,5-Dichlorobenzenesulfenyl chloride (5.1 g.) was isolated as an oil.

EXAMPLE 23

Methyl 5-(2,5-Dichlorophenylthio)pyrrole-3-carboxylate

Under a nitrogen atmosphere, methyl pyrrole-3-carboxylate (2.5 g., 20 mmoles) was dissolved in 50 ml. of methylene chloride and cooled with stirring in an ice-water bath. 2,5-Dichlorobenzenesulfenyl chloride (4.24 g., 20 mmoles) was added dropwise. The bath was removed and the reaction stirred for 1 hour at room temperature, at which time thin layer chromatography (silica gel with ethyl acetate-1/hexane-5/5% acetic acid as eluant) indicated that virtually all of the starting pyrrole ester had been consumed. An equal volume of ether was added, the mixture filtered and the filtrate evaporated in vacuo to a partially crystalline gum (5.2 g.). The latter was recrystallized from methylene chloride/hexane to yield purified methyl 5-(2,5-dichlorophenylthio)pyrrole-3-carboxylate (2.68 g., m.p. 162°–165° C.).

EXAMPLE 24

5-(3,5-Dichlorophenylthio)pyrrole-3-carboxylic Acid

Methyl 5-(3,5-dichlorophenylthio)pyrrole-3-carboxylate (2.5 g.) was combined with 25 ml. of methanol and 25 ml. of 1N sodium hydroxide and refluxed for 3 hours. The methanol was allowed to evaporate, the aqueous residue diluted with approximately one volume of water and washed twice with ether. The aqueous phase was acidified with conc. hydrochloric acid and the product extracted into ethyl acetate. The two ethyl acetate extracts were combined, washed with saturated brine, dried over anhydrous sodium sulfate, filtered and evaporated in vacuo to crude product (1.84 g., m.p. 169°–172° C.). Recrystallization from chloroform afforded purified 5-(3,5-dichlorophenylthio)pyrrole-3-carboxylic acid (1.3 g., m.p. 175°–177° C.).

Analysis: Calcd for $C_{11}H_7O_2NCl_2S$: C, 45.84; H, 2.44; N, 4.86. Found: C, 45.69; H, 2.52; N, 4.85.

EXAMPLE 25

2,4-Dichlorobenzenesulfenyl Chloride

Following the procedure of Example 13, 2,4-dichlorothiophenol (7.16 g., 40 mmoles; Preparation 1) was converted to 2,4-dichlorobenzenesulfenyl chloride (7.5 g., oil).

EXAMPLE 26

Methyl 5-(2,4-Dichlorophenylthio)pyrrole-3-carboxylate

Under nitrogen, methyl pyrrole-3-carboxylate (3.75 g.) was dissolved in 100 ml. of methylene chloride and cooled in an ice-water bath. To the cold, stirred solution, 2,4-dichlorobenzenesulfenyl chloride (6.39 g., 30 mmoles) was added dropwise. The bath was removed and the reaction stirred at room temperature for 1 hour. An equal volume of ether was added, the mixture filtered and the filtrate evaporated in vacuo to crude product (9.0 g., oil). The oil was chromatographed on 300 g. of silica gel with 200 ml. fractions of the ethyl acetate-1/hexane-7 eluant collected. Fractions 6 to 10 were combined and evaporated to yield purified methyl 5-(2,4-dichlorophenylthio)pyrrole-3-carboxylate (3.7 g., solid, m/e 302).

EXAMPLE 27

2-(2,4-Dichlorophenylthio)pyrrole-3-carboxylic Acid

Methyl 5-(2,4-dichlorophenylthio)pyrrole-3-carboxylate (3.6 g.) was combined with 40 ml. of methanol and 40 ml. of 1N sodium hydroxide and refluxed for 2.5 hours. The methanol was allowed to evaporate, the aqueous residue diluted with approximately one volume of water and extracted with ether. The aqueous phase was acidified with conc. hydrochloric acid and the heavy oil which precipitated extracted into ethyl acetate. The ethyl acetate extracts were combined, washed with saturated brine, dried over anhydrous sodium sulfate, filtered and evaporated in vacuo to crude product (3.4 g., m.p. 160°–164° C.). Recrystallization from methanol/water gave purified 5-(2,4-dichlorophenylthio)-pyrrole-3-carboxylic acid (2.3 g., m.p. 166°–168° C.).

Analysis: Calcd. for $C_{11}H_7O_2NCl_2S$: C, 45.84; H, 2.44; N, 4.86. Found: C, 45.68; H, 2.77; N, 5.05.

EXAMPLE 28

3,4-Dichlorobenzenesulfenyl Chloride

By the procedure of Examples 13 and 22, 2,4-dichlorothiophenol (5 g., 279 mmoles) was converted to 3,4-dichlorobenzenesulfenyl chloride (5.0 g., oil).

EXAMPLE 29

Methyl 5-(3,4-Dichlorophenylthio)pyrrole-3-carboxylate

By the procedure of Example 23, methyl pyrrole-3-carboxylate (2.5 g., 20 mmoles) was reacted with 3,4-dichlorobenzenesulfenyl chloride (4.24 g., 20 mmoles) to yield crude product (6.3 g., oil). The crude was chromatographed on 250 g. of silica gel, with 125 ml. fractions of the ethyl acetate-1/hexane-5/5% acetic acid eluant collected. Fractions 2 to 6 were combined and evaporated to dryness to afford purified methyl 5-(3,4-dichlorophenylthio)pyrrole-3-carboxylate (2.76 g., m.p. 93°–96° C.).

EXAMPLE 30

5-(3,4-Dichlorophenylthio)pyrrole-3-carboxylic Acid

Methyl 5-(3,4-dichlorophenylthio)pyrrole-3-carboxylate (1.7 g.) was combined with 20 ml. of methanol and 20 ml. of 1N sodium hydroxide and refluxed for 3 hours. The methanol was allowed to evaporate, and approximately one volume of water was added to the aqueous residue, which was then extracted twice with ether, cooled in an ice-water bath, acidified with conc. hydrochloric acid, and the product extracted into ethyl acetate. The three ethyl acetate extracts were combined, washed with saturated brine, dried over anhydrous sodium sulfate, filtered and evaporated in vacuo to a gummy solid which was crystallized by trituration with hexane and recovered by filtration (1.34 g., m.p. 156°–159° C.). Recrystallization from chloroform gave purified 5-(3,4-dichlorophenylthio)pyrrole-3-carboxylic acid (850 mg., m.p. 159°–161° C.).

Analysis: Calcd for $C_{11}H_7O_2NCl_2S$: C, 45.84; H, 2.44; N, 4.86. Found: C, 45.36; H, 2.58; N, 4.79.

EXAMPLE 31

2,4,5-Trichlorobenzenesulfenyl Chloride

By the procedure of Example 13, 2,4,5-trichlorothiophenol (8.54 g., 40 mmoles) was converted to 2,4,5-trichlorobenzenesulfenyl chloride (8.2 g., oil).

EXAMPLE 32

Methyl 5-(2,4,5-Trichlorophenylthio)pyrrole-3-carboxylate

By the procedure of Example 23, methyl pyrrole-3-carboxylate (2.5 g., 20 mmoles) was reacted with 2,4,5-trichlorobenzenesulfenyl chloride (4.95 g., 20 mmoles) to yield crude product (6.0 g.) as a foam. The crude was chromatographed on 300 g. of silica gel with 200 ml. fractions of the ethyl acetate-1/hexane-7 eluant collected. Fractions 6 to 12 were combined and evaporated to yield methyl 5-(2,4,5-trichlorophenylthio)pyrrole-3-carboxylate (2.2 g., m.p. 165°–175° C.).

EXAMPLE 33

5-(2,4,5-Trichlorophenylthio)pyrrole-3-carboxylic Acid

Methyl 5-(2,4,5-trichlorophenylthio)pyrrole-3-carboxylate (2.1 g.) was combined with 20 ml. of methanol and 20 ml. of 1N sodium hydroxide and heated to reflux. Additional 1N sodium hydroxide was added in an amount sufficient to obtain a solution. Reflux was continued for 2.5 hours, the methanol was then allowed to evaporate, and the aqueous residue was diluted with approximately one volume of water and extracted twice with ether. The aqueous phase was cooled in an ice-water bath and acidified with conc. hydrochloric acid. Crude product (1.65 g., m.p. 210°–215° C.) was recovered by filtration. Recrystallization from methanol/water afforded purified 5-(2,4,5-trichlorophenylthio)pyrrole-3-carboxylic acid (1.01 g., m.p. 215°–217° C.).

Analysis: Calcd. for $C_{11}H_6O_2NCl_3S$: C, 40.95; H, 1.87; N, 4.34. Found: C, 40.56; H, 2.14; N, 4.16.

EXAMPLE 34 p-Fluorobenzenesulfenyl Chloride

Employing the procedure of Example 13, p-fluorothiophenol (5.0 g., 39 mmoles) and N-chlorosuccinimide (5.2 g., 39 mmoles) were reacted to form p-fluorobenzenesulfenyl chloride (4.8 g., oil).

By the same procedure m-fluorothiophenol (Preparation 1) is converted to m-fluorobenzenesulfenyl chloride.

EXAMPLE 35

Methyl 5-(4-fluorophenylthio)pyrrole-3-carboxylate

By the procedure of Example 26, methyl pyrrole-3-carboxylate (2.5 g., 20 mmoles) was reacted with p-fluorobenzenesulfenyl chloride (3.24 g., 20 mmoles), yielding crude product (4.6 g.) as an oil. The crude was chromatographed on 250 g. of silica gel, collecting 125 ml. fractions of the ethyl acetate-1/hexane-5/5% acetic acid eluant. Fractions 5 to 7 were combined and evaporated to yield purified methyl 5-(4-fluorophenylthio)-pyrrole-3-carboxylate (1.5 g., m.p. 100°–105° C., m/e 251).

By the same procedure, m-fluorobenzenesulfenyl chloride is reacted with methyl pyrrole-3-carboxylate to form methyl 5-(3-fluorophenylthio)pyrrole-3-carboxylate.

EXAMPLE 36

5-(4-Fluorophenylthio)pyrrole-3-carboxylic Acid

Methyl 5-(4-fluorophenylthio)pyrrole-3-carboxylate (1.5 g.) was combined with 10 ml. of methanol and 10 ml. of 1N sodium hydroxide and refluxed for 2 hours. The methanol was allowed to evaporate, the aqueous residue was diluted with approximately one volume of water and extracted twice with ether. The aqueous phase was cooled in an ice-water bath and acidified to pH 2.0 with conc. hydrochloric acid. The gummy solid which precipitated was extracted into ethyl acetate. The three combined ethyl acetate extracts were washed with saturated brine, dried over anhydrous sodium sulfate, filtered and evaporated to an oil. Trituration with hexane gave crystalline 5-(4-fluorophenylthio)pyrrole-3-carboxylic acid (1.17 g., m.p. 116–118, m/e 237), recovered by filtration.

Analysis: Calcd. for $C_{11}H_8O_2NFS$: C, 55.68; H, 3.39; N, 5.90. Found: C, 55.78; H, 3.56; N, 5.66.

By the same procedure, methyl 5-(3-fluorophenylthio)pyrrole-3-carboxylate is hydrolyzed to 5-(3-fluorophenylthio)pyrrole-3-carboxylic acid.

EXAMPLE 37 m-Trifluoromethylbenzenesulfenyl Chloride

The procedure of Example 13 was employed to convert m-trifluorothiophenol (7.12 g., 40 mmoles) to m-trifluorobenzenesulfenyl chloride (6.77 g. of oil).

EXAMPLE 38

Methyl 5-(3-Trifluoromethylphenylthio)pyrrole-3-carboxylate

Following the procedure of Example 26, m-trifluorobenzenesulfenyl chloride (6.36 g., 30 mmoles) was reacted with methyl pyrrole-3-carboxylate to yield 9.0 g. of crude product as an oil. The oil was chromatographed identically. Fractions 7 to 9 were combined and evaporated in vacuo to yield purified methyl 5-(3-trifluoromethylphenylthio)pyrrole-3-carboxylate (3.04 g., m.p. 110°–115° C., m/e 301).

EXAMPLE 39

5-(3-Trifluoromethylphenylthio)pyrrole-3-carboxylic Acid

Methyl 5-(3-trifluoromethylphenylthio)pyrrole-3-carboxylate (2.9 g.) was combined with 30 ml. of methanol and 30 ml. of 1N sodium hydroxide and refluxed for 2.5 hours. The methanol was allowed to evaporate and the aqueous residue washed twice with ether. The aqueous phase was acidified with conc. hydrochloric acid and the crude product (2.3 g) which precipitated, was recovered by filtration. Recrystallization of the crude from methanol/water gave purified 5-(3-trifluoromethylphenylthio)pyrrole-3-carboxylic acid (1.47 g., m.p. 138°-140° C.).

Analysis: Calcd. for $C_{12}H_8O_2NF_3S$: C, 50.17; H, 2.80; N, 4.87. Found: C, 49.95; H, 3.06; N, 4.79.

EXAMPLE 40

Pyrrole-3-carboxylic Acid

Methyl pyrrole-3-carboxylate (3 g., 24 mmoles) was combined with 40 ml. of methanol and 40 ml. of 1N sodium hydroxide and refluxed for 1 hour. The methanol was allowed to evaporate, the aqueous residue was diluted with approximately one volume of water and extracted with ether. The aqueous phase was cooled in an ice-water bath and acidified with conc. hydrochloric acid. A small amount of insoluble material was removed by filtration and the filtrate was extracted three times with ethyl acetate. The combined ethyl acetate extracts were back-washed with water and then with saturated brine, dried over anhydrous sodium sulfate, filtered and evaporated to a gummy solid. Trituration with hexane gave crystalline pyrrole-3-carboxylic acid (1.8 g., m.p. 115°-120° C., m/e 111), recovered by filtration.

EXAMPLE 41 p-Methoxybenzenesulfenyl Chloride

Following the procedure of King and Abikar [Can. J. Chem. 46, 9 (1968),], 50 ml. of carbon tetrachloride was cooled to 0°-5° C. in an ice-water bath and saturated with gaseous chlorine. This cold solution was titrated dropwise into a cold (0°-5° C.) solution of p-methoxythiophenol (5 g.) in 25 ml. of carbon tetrachloride in sufficient quantity to maintain a deep red color. The reaction was evporated to an oil. Distillation gave purified p-methoxybenzenesulfenyl chloride (3.59 g., b.p. 107° C./4 mm).

By the same procedure or by the procedure of Example 13, o-methoxythiophenol and m-methoxythiophenol are converted, respectively, to o-methoxybenzenesulfenyl chloride and m-methoxybenzenesulfenyl chloride.

EXAMPLE 42

5-(4-Methoxyphenylthio)pyrrole-3-carboxylic Acid and 4,5-bis(4-methoxyphenylthio)pyrrole-3-carboxylic Acid Under a nitrogen atmosphere, pyrrole-3-carboxylic acid (1.93 g., 17 mmoles) was dissolved in 50 ml. of tetrahydrofuran and cooled in an ice-water bath. To the stirred cold solution, p-methoxysulfenyl chloride (3.0 g., 17 mmoles) was added dropwise. The bath was removed and the reaction was stirred for approximately 16 hours at room temperature. An equal volume of ether was added, the mixture was filtered and the filtrate evaporated in vacuo to yield an oil (4.5 g.). The oil was chromatographed on 250 g. of silica gel, with 200 ml. fractions of the ethyl acetate-1/hexane-5/5% acetic acid eluant collected. Fractions 5 to 7 were combined and evaporated to an oil, which was crystallized from ether/hexane to yield 4,5-bis(4-methoxyphenylthio)pyrrole-3-carboxylic acid (265 mg., m.p. 159°-162° C.).

Analysis: Calcd. for $C_{19}H_{17}O_4NS_2$: C, 58.89; H, 4.42; N, 3.61. Found: C, 58.44; H, 4.27; N, 3.73.

The ether/hexane mother liquor was evaporated to oil, crystallized by trituration with hexane (472 mg.). Recrystallization of the latter from methylene chloride gave 5-(4-methoxyphenylthio)pyrrole-3-carboxylic acid (200 mg., m.p. 144°-147° C.).

Analysis: Calcd. for $C_{12}H_{11}O_3NS$: C, 57.81; H, 4.44; N, 5.61. Found: C, 57.54; H, 4.51; N, 5.46.

The latter product is also prepared by reaction of p-methoxybenzenesulfenyl chloride with methyl pyrrole-3-carboxylate, using the procedures of Example 3, followed by hydrolysis according to Example 4. In this case the chromatography system of the present example is used to purify the product, if necessary.

The same two-step procedure of Examples 3 and 4 is used to convert o-methoxybenzenesulfenyl chloride and m-methoxybenzenesulfenyl chloride to, respectively:
5-(2-Methoxyphenylthio)pyrrole-3-carboxylic acid; and
5-(3-Methoxyphenylthio)pyrrole-3-carboxylic acid.

EXAMPLE 43

Ethylsulfenyl Chloride

Diethyl disulfide (610 mg., 5 mmoles) was dissolved in 10 ml. of carbon tetrachloride. A solution of chlorine in carbon tetrachloride (3.5 ml. of concentration 100 mg./ml.) was added and the solution stirred for 10 minutes at room temperature. The resulting solution, used directly in subsequent steps, was estimated to contain 10 mmoles of ethylsulfenyl chloride.

EXAMPLE 14

Methyl 5-Ethylthiopyrrole-3-carboxylate

Methyl pyrrole-3-carboxylate (1 g., 8 mmoles) was dissolved in 10 ml. of methylene chloride and stirred under nitrogen. A solution of ethylsulfenyl chloride in carbon tetrachloride as prepared above (estimated 10 mmoles) was added, followed by stannic chloride (2.3 ml., 20 mmoles). The reaction mixture was stirred at room temperature for 2 hours. A precipitate formed. A mixture of ice and water (approximately 10 ml.) and ethyl acetate (20 ml.) was added to the reaction mixture, which was then added to 100 ml. of ether. The organic phase was washed twice with 50 ml. of water, once with 50 ml. of 1N sodium hydroxide, twice more with 25 ml. portions of water and finally concentrated to an oil (1 g.). The reaction was repeated on 5.5 times this scale. In this case, the supernatant was decanted from the precipitate which had formed by the end of the reaction period. Water (100 ml.) and ether (approximately 300 ml.) was added to the supernatant. The organic phase was washed with water and concentrated to an oil (1.3 g.). The precipitate was dissolved in 150 ml. of ethyl acetate and 100 ml. of water. The ethyl acetate layer was washed with 50 ml. of water, filtered and concentrated to dryness (4.8 g.). The three crude products above were combined (approximately 6.5 g.), dissolved in approximately 5 ml. of ethyl acetate and chromatographed on 400 ml. of silica gel, eluted with ethyl acetate-1/hexane-6/5% acetic acid. The purification was monitored by thin layer chromatography (silica gel with the same eluant). Middle cuts containing clean product (Rf 0.4) were concentrated to dryness and triturated with hexane to yield slightly gummy crystals (1.15 g.). Recrystallization of 444 mg. of crude from ether/hexane gave purified methyl 5-ethylthiopyrrole-3-carboxylate (140 mg., m.p. 67°–70° C.). Additional crude product (approximately 300 mg.) was recovered by evaporation of the recrystallization mother liquor.

EXAMPLE 45

5-Ethylthiopyrrole-3-carboxylic Acid

Methyl 5-ethylthiopyrrole-3-carboxylic acid (100 mg.) was combined with 5 ml. of ethanol and 5 ml. of 1N sodium hydroxide and heated on a steam bath in an open flask for 1 hour. The aqueous residue was cooled to room temperature and extracted with 2 ml. of ether. The aqueous phase was acidified with conc. hydrochloric acid to yield crystalline 5-ethylthiopyrrole-3-carboxylic acid (38 mg., m.p. 110°–112° C., m/e 171).

Analysis: Calcd. for $C_7H_9O_2NS$: C, 49.11; H, 5.30; N, 8.18. Found: C, 48.96; H, 5.21; N, 7.91.

EXAMPLE 46

Butylsulfenyl Chloride

Under nitrogen, dibutyl disulfide (3.56 g., 20 mmoles) was dissolved in 40 ml. of carbon tetrachloride and the stirred solution cooled in an ice-water bath. A solution of chlorine (1.4 g., 20 mmoles) in 14 ml. of carbon tetrachloride was added dropwise. The bath was removed and the solution stirred for 10 minutes at room temperature. The solution estimated to contain 4.96 g. (40 mmoles) of butylsulfenyl chloride was used directly in subsequent steps.

By the same process, dimethyl disulfide [Hunter and Sorenson, J. Am. Chem. Soc. 54, 3364 (1932)], dipentyl disulfide [Miller et al., J. Am Chem. Soc. 64, 2323 (1942)], and dicyclohexyl disulfide (Preparation 3) are converted respectively, to solutions of methylsulfenyl chloride, pentylsulfenyl chloride and cyclohexylsulfenyl chloride.

EXAMPLE 47

5-Butylthiopyrrole-3-carboxylic Acid

Under nitrogen, pyrrole 3-carboxylic acid (4.44 g., 40 mmoles) was dissolved in 50 ml. of tetrahydrofuran and the solution cooled in an ice-water bath. A solution of butylsulfenyl chloride (Example 46, estimated to contain 4.96 g., 40 mmoles) was added dropwise. The bath was removed and stirring continued for 1 hour at room temperature. An equal volume of ether was added, the mixture was filtered, and the filtrate evaporated to an oil (8.3 g.). The oil was chromatographed on 250 g. silica gel, with 100 ml. fractions of the ethyl acetate-1/toluene-5/5% acetic acid eluant collected. Fraction 9 was evaporated and triturated with carbon tetrachloride to yield crystalline 5-butylthiopyrrole-3-carboxylic acid (185 mg., m/e 199). Fractions 7–8 and 9–10 were combined, evaporated to gums, and rechromatographed in smaller columns, collecting 8 ml. fractions of the ethyl acerate-1/heptane-2 eluant. An additional 114 mg. of 5-butylthiopyrrole-3-carboxylic acid resulted.

Analysis: Calcd. for $C_9H_{13}O_2NS$: C, 54.24; H, 6.57; N, 7.03. Found: C, 54.74; H, 6.94; N, 6.98.

By the same procedure or by the procedures of Examples 44 and 45, methylsulfenyl chloride, pentylsulfenyl chloride, and cyclohexylsulfenyl chloride are used to prepare 5-methylthiopyrrole-3-carboxylic acid, 5-pentylthiopyrrole-3-carboxylic acid, and 5-cyclohexylthiopyrrole-5-carboxylic acid.

EXAMPLE 48

Benzylsulfenyl Chloride

Following the procedure of Example 46, dibenzyl disulfide (4.92 g., 20 mmoles) was converted to a solution estimated to contain 6.32 g. (40 mmoles) of benzylsulfenyl chloride.

EXAMPLE 49

5-Benzylthiopyrrole-3-carboxylic Acid and 4,5-bis-(Benzylthio)pyrrole-3-carboxylic Acid Under nitrogen, pyrrole-3-carboxylic acid (4.44 g., 40 mmoles) was dissolved in 50 ml. of tetrahydrofuran and cooled in an ice-water bath. A solution of benzylsulfenyl chloride (estimated 6.32 g., 40 mmoles) in carbon tetrachloride, freshly prepared by the method of Example 48, was added dropwise to the stirred solution. The bath was removed and the reaction stirred at room temperature for 1 hour. An equal volume of ether was added and the product extracted into 125 ml. of 1N sodium hydroxide. The aqueous phase was backwashed with ether, acidified with conc. hydrochloric acid and the product extracted into ethyl acetate. The three ethyl acetate extracts were combined, backwashed with water, then twice with saturated brine, dried over anhydrous sodium sulfate and evaporated to an oil (8.0 g.). The oil was chromatographed on 300 g. of silica gel, with 200 ml. fractions of the ethyl acetate-1/toluene-5/5% acetic acid collected. Fractions 3 and 4 were combined and evaporated to a gummy solid (2.5 g.). The latter was triturated with hexane and then with ether to yield crystalline 4,5-bis-(benzylthio)pyrrole-3-carboxylic acid (298 mg., m.p. 160°–162° C., m/e 355).

Analysis: Calcd. for $C_{19}H_{17}O_2NS_2$: C, 64.19; H, 4.82; N, 3.94. Found: C, 64.33; H, 4.75; N, 4.34.

The mother liquor from the above crystalline product was evaported to a gum (1.2 g.) and rechromatographed on 50 g. of silica gel, with collection of 50 ml. fractions of the ethyl acetate-1/hexane-5/5% acetic acid eluant. Fractions 6 to 9 were combined, evaporated to a gummy solid, and crystallized from ether/hexane to yield 5-benzylthiopyrrole-3-carboxylic acid (400 mg., m.p. 114°–117° C., m/e 233).

Analysis: Calcd. for $C_{12}H_{11}O_2NS$: C, 61.77; H, 4.75; N, 6.00. Found: C, 61.79; H, 4.83; N, 5.63.

EXAMPLE 50

1-(5-Phenylthio-3-pyrrolyl)methanol

Under nitrogen, 5-phenylthiopyrrole-3-carboxylic acid (1.1 g., 5 mmoles) was dissolved in 30 ml. of tetrahydrofuran. A 1M solution of borane in tetrahydrofuran (10 ml., 10 mmoles) was added dropwise over 1 minute. The reaction was stirred for 13 minutes at room temperature, cooled in an ice-water bath and excess diborane decomposed by careful dropwise addition of 20 ml. of water. Ether (30 ml.) and 10 ml of 1N sodium hydroxide was then added. The organic phase was separated, washed with water and evaporated in vacuo to mixture of oil and crystals (0.8 g.). The reaction was repeated, except that stirring time was reduced to 10 minutes, yielding 1.0 g. of crude product. The two crude products were combined and chromatographed on approximately 200 g. of silica gel eluted with ethyl acetate-1/hexane-1. Purified 1-(5-phenylthio-3-pyrrolyl)methanol (800 mg., m.p. 69°–71° C., m/e 205) was isolated from the last fractions by evaporation, trituration with hexane and filtration.

By the same procedure, other 5-substituted pyrrole-3-carboxylic acids prepared in the Examples above are converted to the corresponding 1-(5-substituted-3-pyrrolyl)methanols, e.g.:

1-(1-Methyl-5-phenylthio-3-pyrrolyl)methanol;
1-[5-(2-Methylphenylthio)-3-pyrrolyl]methanol;
1-[5-(4-Methylphenylthio)-3-pyrrolyl]methanol;
1-[5-(2-Chlorophenylthio)-3-pyrrolyl]methanol;
1-[5-(3-Chlorophenylthio)-3-pyrrolyl]methanol;
1-[5-(4-Chlorophenylthio)-3-pyrrolyl]methanol;
1-[5-(2,5-Dichlorophenylthio)-3-pyrrolyl]methanol;
1-[5-(3,4-Dichlorophenylthio)-3-pyrrolyl]methanol;
1-[5-(2,4,5-Trichlorophenylthio-3-pyrrolyl]methanol;
1-[5-(4-Fluorophenylthio)-3-pyrrolyl]methanol;
1-[5-(3-Trifluoromethylphenylthio)-3-pyrrolyl]methanol;
1-[5-(4-Methoxyphenylthio)-3-pyrrolyl]methanol;
1-(5-Ethylthio-3-pyrrolyl)methanol;
1-(5-Butylthio-3-pyrrolyl)methanol; and
1-(5-Benzylthio-3-pyrrolyl)methanol.

EXAMPLE 51

1-(5-Phenylthio-3-pyrrolyl)methyl Mesylate 1-(5-Phenylthio-3-pyrrolyl)methanol (2.3 g., 11 mmoles) was dissolved in 60 ml. of methylene chloride. Triethylamine (10 ml., 70 mmoles) was added and the solution was cooled to −40° to −45° C. With stirring, methanesulfonyl chloride (4 ml., 51 mmoles) was added dropwise, maintaining the temperature in the same range. The reaction was stirred for 15 minutes at −40° to −45° C. and the cold solution of 1-(5-phenylthio-3-pyrrolyl)methyl mesylate used directly in the next step.

By the same procedure, the other alcohols of Example 50 are converted to the corresponding mesylate esters;

1-(1-Methyl-5-phenylthio-3-pyrrolyl)methyl mesylate;
1-[5-(2-Methylphenylthio)-3-pyrrolyl]methyl mesylate;
1-[5-(4-Methylphenylthio)-3-pyrrolyl]methyl mesylate;
1-[5-(2-chlorophenylthio)-3-pyrrolyl]methyl mesylate;
1-[5-(3-Chlorophenylthio)-3-pyrrolyl]methyl mesylate;
1-[5-(4-Chlorophenylthio)-3-pyrrolyl]methyl mesylate;
1-[5-(2,5-Dichlorophenylthio)-3-pyrrolyl]methyl mesylate;
1-[5-(3,4-Dichlorophenylthio)-3-pyrrolyl]methyl mesylate;
1-[5-(2,4,5-Trichlorophenylthio)-3-pyrrolyl]methyl mesylate;
1-[5-(4-Fluorophenylthio)-3-pyrrolyl]methyl mesylate;
1-[5-(3-Trifluoromethylphenylthio)-3-pyrrolyl]methyl mesylate;
1-[5-(4-Methoxyphenylthio)-3-pyrrolyl]methyl mesylate;
1-(5-Ethylthio-3-pyrrolyl)methyl mesylate;
1-(5-Butylthio-3-pyrrolyl)methyl mesylate; and
1-(5-Benzylthio-3-pyrrolyl)methyl mesylate.

EXAMPLE 52

1-(5-Phenylthio-3-pyrrolyl)methyl Nitrile

Potassium cyanide (2 g.) was dissolved in 5 ml. of water and 30 ml. acetone added—resulting in two phases. The cold (−40° C.), methylene chloride solution of 1-(5-phenylthio-3-pyrrolyl)methyl mesylate of Example 57 (estimated to contain 11 mmoles) was poured into the vigorously stirred, two-phase system. Stirring at room temperature was continued for 30 minutes. The reaction mixture was concentrated in vacuo to remove acetone and methylene chloride. Water (10 ml.) was added to the aqueous residue, and the product was extracted into 25 ml. of ether. The ether was back-washed with 15 ml. of water and evaporated to an oil (200 mg.). The oil was chromatographed on approximately 75 ml. of silica gel, with ethyl acetate-1/hexane-2 as eluant. Evaporation of the initial fractions gave purified 1-(5-phenylthio-3-pyrrolyl)methyl nitrile (157 mg., oil; pnmr/δ: methylene band at 3.50 ppm shifted from 4.35 ppm in the precursor alcohol).

By the same procedure the other mesylate esters of Example 51 are converted to:

1-(1-Methyl-5-phenylthio-3-pyrrolyl)methyl nitrile;
1-[5-(2-Methylphenylthio)-3-pyrrolyl)methyl nitrile;
1-[5-(4-Methylphenylthio)-3-pyrrolyl]methyl nitrile;
1-[5-(2-chlorophenylthio)-3-pyrrolyl]methyl nitrile;
1-[5-(3-Chlorophenylthio)-3-pyrrolyl]methyl nitrile;
1-[5-(4-chlorophenylthio)-3-pyrrolyl]methyl nitrile;
1-[5-(2,5-Dichlorophenylthio)-3-pyrrolyl]methyl nitrile;
1-[5-(3,4-Dichlorophenylthio)-3-pyrrolyl]methyl nitrile;
1-[5-(2,4,5-Trichlorophenylthio)-3-pyrrolyl]methyl nitrile;
1-[5-(4-Fluorophenylthio)-3-pyrrolyl]methyl nitrile;
1-[5-(3-Trifluoromethylphenylthio)-3-pyrrolyl]methyl nitrile;
1-[5-(4-Methoxyphenylthio)-3-pyrrolyl]methyl nitrile;
1-(5-Ethylthio-3-pyrrolyl)methyl nitrile;
1-[5-Butylthio-3-pyrrolyl)methyl nitrile; and
1-[5-Benzylthio-3-pyrrolyl)methyl nitrile.

EXAMPLE 53

2-(5-Phenylthio-3-pyrrolyl)acetic Acid 1-(5-Phenylthio-3-pyrrolyl)methyl nitrile (3.2 g., crude, i.e. material prepared by the method of Example 52 which had not been chromatographed) was combined with 75 ml. of ethanol and 50 ml. of 1N sodium hydroxide and refluxed for 4 hours. The condenser was removed and most of the ethanol evaporated under a stream of nitrogen. The residual solution was diluted with 50 ml. of water and extracted with 50 ml. of ether. The resulting three phases were separated. The upper (ether) phase was discarded. The intermediate phase was diluted with 50 ml. of water, washed with ether and the ether discarded. Both the original lower aqueous phase and the second aqueous phase were acidified with conc. hydrochloric acid and in each case, product extracted into 25 ml. of ethyl acetate, the ethyl acetate backwashed twice with 15 ml. of water and stirred to gummy solid (0.8 g. from the original lower phase; 1.9 g. from the intermediate phase). The crude products were combined and chromatographed on approximately 200 ml. of silica gel, eluted with ethyl acetate-1/hexane-5/5% acetic acid. Evaporation of middle fractions gave purified 2-(5-phenylthio-3-pyrrolyl)acetic acid. (1.50 g., m.p. 125°–127° C.).

Analysis: Calcd. for $C_{12}H_{11}O_2NS$: C, 61.80; H, 4.75; N, 6.01. Found: C, 61.75; H, 4.70; N, 6.04.

By the same procedure the other nitriles of Example 58 are converted to:

2-(1-Methyl-5-phenylthio-3-pyrrolyl)acetic acid;
2-[5-(2-Methylphenylthio)-3-pyrrolyl]acetic acid;
2-[5-(4-Methylphenylthio)-3-pyrrolyl]acetic acid;
2-[5-(2-Chlorophenylthio)-3-pyrrolyl]acetic acid;
2-[5-(3-Chlorophenylthio)-3-pyrrolyl]acetic acid;
2-[5-(4-Chlorophenylthio)-3-pyrrolyl]acetic acid;

2-[5-(2,5-Dichlorophenylthio)-3-pyrrolyl]acetic acid;
2-[5-(3,4-Dichlorophenylthio)-3-pyrrolyl]acetic acid;
2-[5-(2,4,5-Trichlorophenylthio)-3-pyrrolyl]acetic acid;
2-[5-(4-Fluorophenylthio)-3-pyrrolyl]acetic acid;
2-[5-(3-Trifluoromethylphenylthio)-3-pyrrolyl]acetic acid;
2-[5-(4-Methoxyphenylthio)-3-pyrrolyl]acetic acid;
2-(5-Ethylthio-3-pyrrolyl)acetic acid;
2-(5-Butylthio-3-pyrrolyl)acetic acid; and
2-(5-Benzylthio-3-pyrrolyl)acetic acid.

EXAMPLE 54

2-Phenylthiopyrrole

Pyrrole (2.0 g., 30 mmoles) was dissolved in 20 ml. of ether. Benzenesulfenyl chloride (4.5 g., 30 mmoles) was added dropwise at such a rate that the purple color of the reagent was discharged. A slightly exothermic reaction was noted. After addition was complete (10 minutes), the reaction was evaporated to an oil (5.7 g.). The oil was chromatographed on approximately 180 ml. of silica gel, eluted with ethyl acetate-1/hexane-7. Middle fractions, evaporated to dryness, afforded 2-phenylthiopyrrole (300 mg.).

Analysis: Calcd. for $C_{10}H_9NS$: C, 68.56; H, 5.18; N, 8.00. Found: C, 68.15; H, 5.27; N, 7.83.

By the same procedure, the sulfenyl chlorides of the above examples are reacted with pyrrole or with a 1-alkylpyrrole (Example 5) to form the corresponding 2-substituted pyrroles, e.g.:
1-Methyl-2-phenylthiopyrrole;
2-(2-Methylphenylthio)pyrrole;
2-(4-Methylphenylthio)pyrrole;
2-(2-Chlorophenylthio)pyrrole;
2-(3-Chlorophenylthio)pyrrole;
2-(4-Chlorophenylthio)pyrrole;
2-(2,5-Dichlorophenylthio)pyrrole;
2-(3,4-Dichlorophenylthio)pyrrole;
2-(2,4,5-Trichlorophenylthio)pyrrole;
2-(4-Fluorophenylthio)pyrrole;
2-(4-Methoxyphenylthio)pyrrole;
2-Ethylthiopyrrole;
2-Butylthiopyrrole; and
2-Benzylthiopyrrole.

EXAMPLE 55

2-Phenylthio-5-trichloroacetylpyrrole

2-Phenylthiopyrrole (1.75 g., 10 mmoles) was dissolved in 20 ml. of methylene chloride. Trichloroacetyl chloride (1.1 ml., 10 mmoles) was added and the reaction stirred for 3 hours at room temperature. The reaction mixture was washed with 20 ml. of water and concentrated to yield 2-phenylthio-5-trichloroacetylpyrrole, used directly in the next step.

By this procedure the other 2-substituted pyrroles of Example 54 are converted to:
1-Methyl-2-phenylthio-5-trichloroacetylpyrrole;
2-(2-Methylphenylthio)-5-trichloroacetylpyrrole;
2-(4-Methylphenylthio)-5-trichloroacetylpyrrole;
2-(2-Chlorophenylthio)-5-trichloroacetylpyrrole;
2-(3-Chlorophenylthio)-5-trichloroacetylpyrrole;
2-(4-Chlorophenylthio)-5-trichloroacetylpyrrole;
2-(2,5-Dichlorophenylthio)-5-trichloroacetylpyrrole;
2-(3,4-Dichlorophenylthio)-5-trichloroacetylpyrrole;
2-(2,4,5-Trichlorophenylthio)-5-trichloroacetylpyrrole;
2-(4-Fluorophenylthio)-5-trichloroacetylpyrrole;
2-(4-Methoxyphenylthio)-5-trichloroacetylpyrrole;
2-Ethylthio-5-trichloroacetylpyrrole;
2-Butylthio-5-trichloroacetylpyrrole; and
2-Benzylthio-5-trichloroacetylpyrrole.

EXAMPLE 56

5-Phenylthiopyrrole-2-carboxylic Acid

2-Phenylthiopyrrole-5-trichloroacetylpyrrole (estimated 10 mmoles, the entire product from Example 57) was combined with 25 ml. of 1N sodium hydroxide and 60 ml of methanol and refluxed for one hour. The condenser was removed and most of the methanol removed by boiling (approximately 20 minutes). The reaction mixture was cooled to room temperature and by-products removed by filtration. The filtrate was extracted with 25 ml. of ether, the aqueous phase acidified with conc. hydrochloric acid and the product extracted into 35 ml of ethyl acetate. The ethyl acetate phase was backwashed with water and concentrated to a solid (0.7 g.). Recrystallization from ether/hexane gave purified 5-phenylthiopyrrole-2-carboxylic acid (475 mg., m.p. 129°–131° C., m/e 219).

Analysis: Calcd. for $C_{11}H_9O_2NS$: C, 60.27; H, 4.14; N, 6.39. Found: C, 60.37; H, 4.08; N, 6.37.

A second crop of product was also obtained (190 mg., m.p. 126°–128° C.).

By the same procedure, the other substituted pyrroles of Example 55 are converted to:
1-Methyl-5-phenylthiopyrrole-2-carboxylic acid;
5-(2-Methylphenylthio)pyrrole-2-carboxylic acid;
5-(4-Methylphenylthio)pyrrole-2-carboxylic acid;
5-(2-Chlorophenylthio)pyrrole-2-carboxylic acid;
5-(3-Chlorophenylthio)pyrrole-2-carboxylic acid;
5-(4-Chlorophenylthio)pyrrole-2-carboxylic acid;
5-(2,5-Dichlorophenylthio)pyrrole-2-carboxylic acid;
5-(3,4-Dichlorophenylthio)pyrrole-2-carboxylic acid;
5-(2,4,5-Trichlorophenylthio)pyrrole-2-carboxylic acid;
5-(4-Fluorophenylthio)pyrrole-2-carboxylic acid;
5-(4-Methoxyphenylthio)pyrrole-2-carboxylic acid;
5-Ethylthiopyrrole-2-carboxylic acid;
5-Butylthiopyrrole-2-carboxylic acid; and
5-Benzylthiopyrrole-2-carboxylic acid.

EXAMPLE 57

1-Methyl-5-phenylthio-2-pyrrolylmethyl Nitrile

Under nitrogen, 1-methyl-2-pyrrolylmethyl nitrile (12 g., 0.1 mole) was dissolved in 250 ml. of methylene chloride and cooled with stirring in an ice-water bath. A solution of benzenesulfenyl chloride (estimated 14.4 g., 0.1 mole) in 125 ml. of methylene chloride was added dropwise. The bath was removed and the reaction stirred at room temperature for 1 hour. An equal volume of ether was added, the reaction extracted twice with water, and the organic layer evaporated to an oil (23 g.). The oil was chromatographed on 300 g. of silica gel, with 250 ml, fractions of the ethyl acetate-2/hexane-7 eluant collected. Fraction 2 was evaporated to yield 1-methyl-5-phenylthio-2-pyrrolylmethyl nitrile (9.0 g., oil; Rf 0.25 on thin layer chromatography on silica gel with ethyl acetate-2/hexane-7 as eluant.

By the same procedure, the other sulfenyl chlorides of the above examples are reacted with 2-pyrrolylmethyl nitrile, 1-methyl-2-pyrrolylmethyl nitrile or other 1-alkyl-2-pyrrolylmethyl nitriles as appropriate to yield 5-substituted-2-pyrrolylmethyl nitriles, e.g.:
5-Phenylthio-2-pyrrolyl nitrile;
1-Ethyl-5-phenylthio-2-pyrrolyl nitrile;
5-(2-Methylphenylthio)-2-pyrrolyl nitrile;
5-(4-Methylphenylthio)-2-pyrrolyl nitrile;

5-(2-Chlorophenylthio)-2-pyrrolyl nitrile;
5-(3-Chlorophenylthio)-2-pyrrolyl nitrile;
5-(4-Chlorophenylthio)-2-pyrrolyl nitrile;
5-(2,5-Dichlorophenylthio)-2-pyrrolyl nitrile;
5-(3,4-Dichlorophenylthio)-2-pyrrolyl nitrile;
5-(2,4,5-Trichlorophenylthio)-2-pyrrolyl nitrile;
5-(4-Fluorophenylthio)-2-pyrrolyl nitrile;
5-(4-Methoxyphenylthio)-2-pyrrolyl nitrile;
5-Ethylthio-2-pyrrolyl nitrile;
5-Butylthio-2-pyrrolyl nitrile; and
5-Benzylthio-2-pyrrolyl nitrile.

The 2-pyrrolylmethyl nitriles required for the above syntheses, when not available commercially or in the literature, are derived from pyrrole-2-carboxylic acid by the procedures of Examples 50 to 52 and 5, i.e., diboran reduction, mesylate ester formation, conversion to nitrile and, if required, alkylation.

EXAMPLE 58

2-(1-Methyl-5-phenylthio-2-pyrrolyl)acetic Acid

1-Methyl-5-phenylthio-2-pyrrolylmethyl nitrile (2.0 g.) was combined with 20 ml. of 5N sodium hydroxide and 20 ml. of ethanol and refluxed for 2 hours. The ethanol was allowed to evaporate and the aqueous residue was diluted with approximately one volume water, washed twice with ether, cooled in an ice-water bath, acidified with conc. hydrochloric acid and the product extracted into ethyl acetate. The three ethyl acetate extractions were combined, dried over anhydrous sodium sulfate, and evaporated to crude product (1.5 g.). Recrystallization from ether/hexane afforded purified 2-(1-methyl-5-phenylthio-2-pyrrolyl)acetic acid (770 mg., m.p. 94°–96° C., m/e 247).

Analysis: Calcd. for $C_{13}H_{13}O_2NS$: C, 63.13; H, 5.29; N, 5.66. Found: C, 63.31; H, 5.33; N, 5.62.

By the same procedure, the other 5-substituted-2-pyrrolylmethyl nitriles of Example 57 are converted to:
2-(5-Phenylthio-2-pyrrolyl)acetic acid;
2-(1-Ethyl-5-phenylthio-2-pyrrolyl)acetic acid;
2-[5-(2-Methylphenylthio)-2-pyrrolyl]acetic acid;
2-[5-(4-Methylphenylthio)-2-pyrrolyl]acetic acid;
2-[5-(2-Chlorophenylthio)-2-pyrrolyl]acetic acid;
2-[5-(3-Chlorophenylthio)-2-pyrrolyl]acetic acid;
2-[5-(4-Chlorophenylthio)-2-pyrrolyl]acetic acid;
2-[5-(2,5-Dichlorophenylthio)-2-pyrrolyl]acetic acid;
2-[5-(3,4-Dichlorophenylthio)-2-pyrrolyl]acetic acid;
2-[5-(2,4,5-Trichlorophenylthio)-2-pyrrolyl]acetic acid;
2-[5-(4-Fluorophenylthio)-2-pyrrolyl]acetic acid;
2-[5-(4-Methoxyphenylthio)-2-pyrrolyl]acetic acid;
2-(5-Ethylthio-2-pyrrolyl)acetic acid;
2-(5-Butylthio-2-pyrrolyl)acetic acid; and
2-(5-Benzylthio-2-pyrrolyl)acetic acid.

EXAMPLE 59

4-Phenylthiopyrrole-2-carboxylic Acid

Pyrrole-2-carboxylic acid (5.5 g., 50 mmoles) was dissolved to the extent of about 90% by warming in 200 ml. of tetrahydrofuran. The stirred, partial solution was cooled to −34° C., and freshly prepared benzenesulfenyl chloride (7.5 g., 52 mmoles) added at this temperature. The reaction mixture was gradually warmed to room temperature over approximately 2.5 hours and left to stir at room temperature for approximately 64 hours. Insoluble material was removed by filtration. The filtrate was diluted with 200 ml. of ether and the product extracted into 150 ml. of 1N sodium hydroxide. The aqueous phase was back-washed with 75 ml. of ether, acidified with conc. hydrochloric acid and the product extracted into 75 ml. of ether. The ether was back-washed with 50 ml. of water, concentrated to dryness (9.0 g.), the residue taken back up in 30 ml. of ether, insolubles (0.6 g., mostly starting material) removed by filtration, and reconcentrated to crude product (8 g.). The latter was chromatographed on approximately 350 g. of silica gel, with approximately 25 ml. fractions of the ethyl acetate-1/hexane-7/5% acetic acid eluant collected. Fractions, concentrated to dryness, were monitored by thin layer chromatography employing the same eluant. Late fractions, including some containing a little starting material, were combined and recrystallized from ether/hexane to yield purified 4-phenylthiopyrrole-2-carboxylic acid (0.34 g., m.p. 181°–183° C., m/e 219).

Analysis: Calcd. for $C_{11}H_9O_2NS$: C, 60.27; H, 4.14; N, 6.39. Found: C, 60.58; H, 4.24; N, 6.53.

EXAMPLE 60

4-(4-Chlorophenylthio)pyrrole-2-carboxylic Acid

Pyrrole-2-carboxylic acid (7.8 g., 70 mmoles) was for the most part dissolved in 350 ml. of tetrahydrofuran by stirring at room temperature. The partial solution was cooled with stirring to −40° C. p-Chlorobenzenesulfenyl chloride (13 g., 72 mmoles) was added at −40° C. and the reaction allowed to warm to room temperature gradually over a 3 hour period. The reaction mixture was left to stand for approximately 64 hours. The reaction mixture was diluted with 200 ml. of ether and extracted with 125 ml. of 1N sodium hydroxide, from which 5 g. of crude product was isolated by acidification, extracted into ethyl acetate and concentrated to dryness. Pure product was obtained by extraction of the above tetrahydrofuran-ether phase with 50 ml. of water, acidification of the aqueous phase with conc. hydrochloric acid, extraction of product into 50 ml. of ethyl acetate, back-wash with water and concentration of the ethyl acetate to dryness, yielding 5.7 g. of crude product. Two-fold recrystallization of the latter from acetone-hexane afforded pure 4-(4-chlorophenylthio)pyrrole-2-carboxylic acid (908 mg. in two crops; m.p. 218°–220° C., m/e 253).

Analysis: Calcd. for $C_{11}H_8O_2NSCl$: C, 52.07; H, 3.18; N, 5.52. Found: C, 52.11; H, 3.32; N, 5.31. C, 52.13; H, 3.41; N, 5.25.

By the procedures of Examples 59 and 60, other sulfenyl chlorides, as prepared in the Examples above, are reacted with pyrrole-2-carboxylic acid to prepare the corresponding 4-substituted pyrrole-2-carboxylic acids, e.g.:
4-(2-Methylphenylthio)pyrrole-2-carboxylic acid;
4-(4-Methylphenylthio)pyrrole-2-carboxylic acid;
4-(2-Chlorophenylthio)pyrrole-2-carboxylic acid;
4-(3-Chlorophenylthio)pyrrole-2-carboxylic acid;
4-(2,5-Dichlorophenylthio)pyrrole-2-carboxylic acid;
4-(3,4-Dichlorophenylthio)pyrrole-2-carboxylic acid;
4-(2,4,5-Trichlorophenylthio)pyrrole-2-carboxylic acid;
4-(4-Fluorophenylthio)pyrrole-2-carboxylic acid;
4-(3-Trifluoromethylphenylthio)pyrrole-2-carboxylic acid;
4-(4-Methoxyphenylthio)pyrrole-2-carboxylic acid;
4-Ethylthiopyrrole-2-carboxylic acid;
4-Butylthiopyrrole-2-carboxylic acid; and
4-Benzylthiopyrrole-2-carboxylic acid.

The acids produced by the procedure of this Example are converted to the corresponding 1-alkyl derivatives by application of the alkylation procedure of Example 5 thereto, followed by the hydrolysis of the resulting 1-alkyl alkyl ester according to the procedure of Example 6.

The acids produced by the procedure of this Example are converted to the corresponding 2-(4-substituted-2-pyrrolyl)acetic acids by application thereto of the diborane reduction, mesylate ester formation, conversion to nitrile and hydrolysis sequence of Examples 50 to 53.

EXAMPLE 61

1-Methyl-4,5-bis(phenylthio)pyrrole-2-carboxylic Acid

1-Methylpyrrole-2-carboxylic acid (5 g., 40 mmoles) was dissolved in 50 ml. of methylene chloride. Benzenesulfenyl chloride (12 g., 80 mmoles) was added portionwise over approximately 2 1 minutes. The resulting reaction mixture was stirred for 4.5 hours at room temperature. 1-Methyl-4,5-bis(phenylthio)pyrrole-2-carboxylic acid (1.5 g., m.p. 172°–174° C., m/e 341) was recovered directly from the reaction mixture. A second crop was obtained from the mother liquor by diluting with 2 volumes of ether, extraction of the product into 50 ml. of 1N sodium hydroxide and acidification of the aqueous phase (0.70 g., m.p. 172°–174° C.).

Analysis: Calcd. for $C_{18}H_{15}NO_2S_2$: C, 63.34; H, 4.43; N, 4.10. Found: C, 62.94; H, 4.35; N, 4.34.

By replacing 1-methylpyrrole-2-carboxylic acid with an equivalent amount of 1-ethylpyrrole-2-carboxylic acid, the procedure of this example produces 1-ethyl-4,5-bis-(phenylthio)pyrrole-2-carboxylic acid.

EXAMPLE 62

Methyl 5-Benzoylpyrrole-3-carboxylate

Under nitrogen, methyl pyrrole-3-carboxylate (5 g., 40 mmoles) was combined with benzoyl chloride (4.8 ml., 40 mmoles) and stannic chloride (9.2 ml. 80 mmoles) in 75 ml. of methylene chloride and stirred for 3 hours at room temperature. Ice and water (50 ml.) was added slowly and stirring continued for an additional 15 minutes. Ether (150 ml.) was then added and, after equilibration, the phases separated. The upper, organic phase was washed sequentially with 50 ml. of water, 50 ml. of 1N sodium hydroxide and 50 ml. of water, and evaporated to dryness to yield crude product (6.4 g. of solid). Recrystallization from acetonehexane gave purified methyl 5-benzoylpyrrole-3-carboxylate (4.1 g., Rf 0.4 on silica gel thin layer chromatography eluted with ethyl acetate-1/hexane-5/5% acetic acid).

Belgian patent 870,910 (published Mar. 29, 1979) also discloses, in a general fashion, that Friedel-Crafts acylation of pyrrole-3-carboxylates yields 5-acylpyrrole-3-carboxylates. This patent specifically exemplifies preparation of methyl 1-methyl-5-(3-chlorobenzoyl)pyrrole-3-carboxylate (see Example 84 below).

EXAMPLE 63

5-Benzoylpyrrole-3-carboxylic Acid

Methyl 5-benzoylpyrrole-3-carboxylate (7.5 g.) was combined with 100 ml. of 1N sodium hydroxide and 100 ml. of ethanol and boiled in an open flask for 1 hour, by which time most of the ethanol had evaporated. The aqueous residue was diluted with 100 ml. of water and acidified with conc. hydrochloric acid to precipitate crystalline 5-benzoylpyrrole-3-carboxylic acid [6.3 g., m.p. 289°–290° C. (dec.), m/e 215].

Belgian patent 870,910 (cited above) discloses preparation of analogous acids by hydrolysis of the corresponding ester.

EXAMPLE 64

Methyl 5-(2-Methylbenzoyl)pyrrole-3-carboxylate

Under nitrogen at room temperature, methyl pyrrole-3-carboxylate (2.5 g., 20 mmoles) was combined with 75 ml. of methylene chloride. o-Toluoyl chloride (3.09 g., 20 mmoles) in 25 ml. of methylene chloride was added, followed by stannic chloride (4.6 ml., 40 mmoles) added at a fast dropwise rate via a needle and syringe. Progress of the reaction was followed by thin layer chromatography (silica gel with ethyl acetate-1/hexane-5/5% acetic acid as eluant). After stirring at room temperature for 2.5 hours, the reaction was cooled with an ice-water bath while 75 ml. of water was added dropwise. After addition was complete, the mixture was stirred for 15 minutes at room temperature, approximately an equal volume of ether was added, the organic layer separated, washed in sequence with water, 1N sodium hydroxide, water and saturated brine, dried over anhydrous sodium sulfate, filtered and evaporated to yield methyl 5-(2-methylbenzoyl)pyrrole-3-carboxylate.

EXAMPLE 65

5-(2-Methylbenzoyl)pyrrole-3-carboxylic Acid

Methyl 5-(2-methylbenzoyl)pyrrole-3-carboxylic acid (3.6 g.) was combined with 40 ml. of methanol and 40 ml. of 1N sodium hydroxide, refluxed for 2.5 hours, the methanol evaporated, the aqueous residue diluted with approximately one volume of water and extracted with ether. The aqueous phase was cooled and acidified with conc. hydrochloric acid to yield crude product (4.0 g.), recovered by filtration. Recrystallization from methanol afforded purified 5-(2-methylbenzoyl)pyrrole-3-carboxylic acid (2.2 g., m.p. 280°–282° C.).

Analysis: Calcd. for $C_{13}H_{11}O_3N$: C, 68.11; H, 4.83; N, 6.11. Found: C, 68.34; H, 4.97; N, 6.16.

EXAMPLE 66

Methyl 5-(4-Methylbenzoyl)pyrrole-3-carboxylate

Following the procedure of Example 64, p-toluoyl chloride (3.09 g., 20 mmoles) and methyl pyrrole-3-carboxylate were reacted to form methyl 5-(4-methylbenzoyl)pyrrole-3-carboxylate (2.9 g., m.p. 155°–159° C., m/e 243).

By the same procedure, equivalent amounts of m-toluoyl chloride, o-fluorobenzoyl chloride, m-fluorobenzoyl chloride, p-fluorobenzoyl chloride, o-chlorobenzoyl chloride, m-chlorobenzoyl chloride, and p-chlorobenzoyl chloride are reacted with methyl pyrrole-3-carboxylate to produce, respectively:
Methyl 5-(3-methylbenzoyl)pyrrole-3-carboxylate;
Methyl 5-(2-fluorobenzoyl)pyrrole-3-carboxylate;
Methyl 5-(3-fluorobenzoyl)pyrrole-3-carboxylate;
Methyl 5-(4-fluorobenzoyl)pyrrole-3-carboxylate;
Methyl 5-(2-chlorobenzoyl)pyrrole-3-carboxylate;
Methyl 5-(3-chlorobenzoyl)pyrrole-3-carboxylate;
Methyl 5-(4-chlorobenzoyl)pyrrole-3-carboxylate;

EXAMPLE 67

5-(4-Methylbenzoyl)pyrrole-3-carboxylic Acid

Methyl 5-(4-methylbenzoyl)pyrrole-3-carboxylate (2.7 g.) was refluxed for 2 hours with 30 ml. of methanol and 30 ml. of sodium hydroxide, and the product isolated by the procedure of Example 65. The crude product (3.23 g.) was recrystallized from methanol to produce purified 5-(4-methylbenzoyl)pyrrole-3-carboxylic acid (1.32 g., m.p. 275°–277° C.).

Analysis: Calcd, for $C_{13}H_{11}O_3N$: C, 68.11; H, 4.83; N, 6.11. Found: C, 67.95; H, 4.95; N, 6.07.

By the same procedure, the other esters of Example 66 are converted to:
5-(3-Methylbenzoyl)pyrrole-3-carboxylic acid;
5-(2-Fluorobenzoyl)pyrrole-3-carboxylic acid;
5-(3-Fluorobenzoyl)pyrrole-3-carboxylic acid;
5-(4-Fluorobenzoyl)pyrrole-3-carboxylic acid;
5-(2-Chlorobenzoyl)pyrrole-3-carboxylic acid;
5-(3-Chlorobenzoyl)pyrrole-3-carboxylic acid; and
5-(4-Chlorobenzoyl)pyrrole-3-carboxylic acid.

EXAMPLE 68

2-(4-Chlorobenzoylmethyl)imidazo[3,4-a]pyridinium Bromide

Imidazo[3,4-a]pyridine (8.3 g., 70 mmoles) dissolved in 125 ml. of ether was mixed with p-chlorophenacyl bromide (16.3 g., 70 mmoles) dissolved in 50 ml. of tetrahydrofuran and stirred at room temperature for 10 minutes at which time a gummy precipitate (approximately 2 g.) was separated by decantation. The decant was stirred for an additional 22 hours at room temperature, by which time product had precipitated heavily. Filtration with ether wash gave 2-(4-chlorobenzoylmethyl)imidazo[3,4-a]pyridinium bromide (16.8 g., m.p. 241°–243° C.).

By the same procedure, imidazo[3,4-a]pyridine is reacted with phenacyl bromide, p-fluorophenacyl chloride, and p-methylphenacyl bromide to yield, respectively:
2-Benzoylmethylimidazo[3,4-a]pyridinium bromide;
2-(4-Fluorobenzoylmethylimidazo[3,4-a]pyridinium chloride; and
2-(4-Methylbenzoylmethylimidazo[3,4-a]pyridinum bromide.

EXAMPLE 69

Ethyl 1-(2-Pyridylmethyl)-5-(4-chlorobenzoyl)pyrrole-3-carboxylate Hydrochloride 2-(4-Chlorobenzoyl)imidazo[3,4-a]pyridinium bromide (10.5 g., 30 mmoles) was stirred with potassium carbonate (16.5 g., 120 mmoles) in 125 ml. of dimethylformamide for 45 minutes at room temperature. The mixture was cooled to −10° C., and ethyl propiolate (4.65 ml., 35 mmoles) was added. The temperature rose to 0° C. The reaction mixture was then warmed to room temperature, stirred for 4 hours, and filtered. The filtrate was diluted with 250 ml. of ether and extracted with two 250 ml. portions of water. The water extracts were combined and back-washed with 250 ml. of ether. The original organic layer and the ether back-wash were combined, dried over anhydrous sodium sulfate, and concentrated to an oil. The oil was dissolved in 150 ml. of ether. Hexane (150 ml.) was added and a precipitate removed by filtration. Addition of excess hydrogen chloride in ethyl acetate to the filtrate precipitated crystalline ethyl 1-(2-pyridylmethyl)-2-(4-chlorobenzoyl)-pyrrole-4-carboxylate hydrochloride (5.1 g., m.p. 179°–182° C.).

By the same procedure, the other pyridinium halides of Example 68 are converted to:

Ethyl 1-(2-pyridylmethyl)-5-(benzoyl)pyrrole-3-carboxylate hydrochloride.
Ethyl 1-(2-pyridylmethyl)-5-(4-fluorobenzoyl)pyrrole-3-carboxylate hydrochloride; and
Ethyl 1-(2-pyridylmethyl)-5-(4-methylbenzoyl)pyrrole-3-carboxylate hydrochloride.

EXAMPLE 70

Ethyl 5-(4-Chlorobenzoyl)pyrrole-3-carboxylate

Ethyl 1-(2-pyridylmethyl)-5-(4-chlorobenzoyl)pyrrole-3-carboxylate hydrochloride (4.05 g.) was combined with 150 ml. of dioxane, 5 ml. of water and 10 g. of selenium dioxide and refluxed for 18 hours. The reaction mixture was filtered, the filtrate diluted with 150 ml. of ether and 150 ml. of water, and equilibrated. The organic phase was separated, back-washed with two 100 ml. portions of water, and concentrated to yield solid ethyl 5-(4-chlorobenzoyl)pyrrole-3-carboxylate (2.7 g., Rf 0.55 on silica gel thin layer chromatography with ethyl acetate-1/hexane-5/5% acetic acid as eluant).

By the same procedure, the other 1-(2-pyridylmethyl)pyrroles of Example 69 are converted to:
Ethyl 5-benzoylpyrrole-3-carboxylate;
Ethyl 5-(4-fluorobenzoyl)pyrrole-3-carboxylate; and
Ethyl 5-(4-methylbenzoyl)pyrrole-3-carboxylate.

EXAMPLE 71

5-(4-Chlorobenzoyl)pyrrole-3-carboxylic Acid

Ethyl 5-(4-chlorobenzoyl)pyrrole-3-carboxylate (0.7 g.) was combined with 20 ml. of methanol and 15 ml. of 1N sodium hydroxide and boiled in an open flask for 1 hour. Most of the methanol evaporated. The mixture was diluted to 40 ml. with water, treated with activated charcoal, and acidified to yield 5-(4-chlorobenzoyl)pyrrole-3-carboxylic acid [550 mg., m.p. 278°–280° C. (dec)]. Recrystallization from 1:1 methanol-acetone gave two crops of purified product [385 mg., m.p. 280°–282° C. (dec)].

Analysis: Calcd. for $C_{12}H_8O_3NCl$: C, 57.73; H, 3.23; N, 5.61. Found: C, 57.50; H, 3.15; N, 5.42.

By the same procedure, the other ethyl esters of Example 70 are converted to:
5-Benzoylpyrrole-3-carboxylic acid;
5-(4-Fluorobenzoyl)pyrrole-3-carboxylic acid; and
5-(4-Methylbenzoyl)pyrrole-3-carboxylic acid.

EXAMPLE 72

Methyl 5-(2,4-Dichlorobenzoyl)pyrrole-3-carboxylate

By the procedure of Example 64, 2,4-dichlorobenzoyl chloride (4.18 g., 20 mmoles) and methyl pyrrole-3-carboxylate were reacted to form methyl 5-(2,4-dichlorobenzoyl)pyrrole-3-carboxylate (3.0 g., gummy solid, Rf 0.5 on silica gel thin layer chromatography with ethyl acetate-1/hexane-1 as eluant).

EXAMPLE 73

5-(2,4-Dichlorobenzoyl)pyrrole-3-carboxylic Acid

Methyl 5-(2,4-dichlorobenzoyl)pyrrole-3-carboxylate (3.0 g.) was refluxed for 2.5 hours in 35 ml. of methanol and 35 ml. of 1N sodium hydroxide. The methanol was evaporated, and approximately one volume of water was added to the aqueous residue. The mixture was extracted twice with ether, and acidified with conc. hydrochloric acid to yield 2.12 g. of crude product, recovered by filtration. Recrystallization from methanol, which included an activated carbon treatment, afforded purified 5-(2,4-dichlorobenzoyl)pyrrole-3-carboxylic acid (1.06 g., m.p. 245°–249° C.).

Analysis: Calcd. for $C_{12}H_7O_3NCl_2$: C, 50.73; H, 2.48; N, 4.93. Found: C, 50.66; H, 2.69; N, 4.87.

EXAMPLE 74

Methyl 5-(3,5-Dimethoxybenzoyl)pyrrole-3-carboxylate

By the procedure of Example 64, but a 5 hour reaction time, 3,5-dimethoxybenzoyl chloride (4.0 g., 20 mmoles) was reacted with methyl pyrrole-3-carboxylate to yield, without recrystallization, methyl 5-(3,5-dimethoxybenzoyl)pyrrole-3-carboxylate (3.7 g., m.p. 115°–120° C., m/e 289).

EXAMPLE 75

5-(3,5-Dimethoxybenzoyl)pyrrole-3-carboxylic Acid

Methyl 5-(3,4-dimethoxybenzoyl)pyrrole-3-carboxylate (3.7 g.) was refluxed with 40 ml. of methanol and 40 ml. of 1N sodium hydroxide with 2 hours and isolated by the procedure of Example 73. Recrystallization from methanol gave purified 5-(3,5-dimethoxybenzoyl)pyrrole-3-carboxylic acid (1.5 g., m.p. 267°–269° C.).

Analysis: Calcd. for $C_{14}H_{13}O_5N$: C, 61.08; H, 4.75; N, 5.08. Found: C, 60.65; H, 4.72; N, 5.11.

EXAMPLE 76

2-(4-Phenylbenzoylmethyl)imidazo[3,4-a]pyridinium Bromide

Imidazo[3,4-a]pyridine (7.1 g., 60 mmoles), dissolved in 150 ml. of ether, was mixed with p-phenylphenacyl bromide dissolved in 100 ml. of tetrahydrofuran and stirred for 4 hours at room temperature. A first crop of crystalline 2-(4-phenylbenzoylmethyl)imidazo[3,4-a]pyridinium bromide [7.8 g., m.p. 258°–260° C. (dec.)] was recovered by filtration. After standing four days at room temperature, a second crop of crystallized product [9.5 g., m.p. 262°–264° C. (dec.)] was recovered from the filtrate.

EXAMPLE 77

Ethyl 1-(2-Pyridylmethyl-5-(4-phenylbenzoyl)pyrrole-3-carboxylate Hydrochloride 2-(4-Phenylbenzoylmethyl)imidazo[3,4-a]pyridinium bromide (16 g., 40 mmoles), potassium carbonate (22 g., 160 mmoles) and ethyl propiolate (6.4 ml., 48 mmoles) was combined according to the procedure of Example 69, stirred for approximately 16 hours at room temperature, then isolated and converted to hydrochloride according to the procedure of Example 69, to yield ethyl 1-(2-pyridylmethyl)-5-(4-phenylbenzoyl)pyrrole-3-carboxylate (5.3 g., intermediate Rf on silica gel thin layer chromatography with ethyl acetate/5% acetic acid as eluant).

EXAMPLE 78

Ethyl 5-(4-Phenylbenzoyl)pyrrole-3-carboxylate

Ethyl 1-(2-pyridylmethyl)-5-(4-phenylbenzoyl)pyrrole-3-carboxylate (5.3 g.) was combined with 150 ml. of dioxane, 5 ml. of water and 10 g. of selenium dioxide and refluxed for approximately 16 hours. Insoluble material was separated by filtration, the filtrate was diluted with 150 ml. of ether and 150 ml. of water, the mixture equilibrated, the ether phase separated, back-washed twice with 100 ml. portions of water, filtered and concentrated to yield ethyl 5-(4-phenylbenzoyl)pyrrole-3-carboxylate (3.1 g, solid; Rf 0.4 on silica gel thin layer chromatography with ethyl acetate-1/hexane-5/5% acetic acid as eluant).

By following the procedure of Examples 64, 66, 68 and 74, 4-phenylbenzoyl chloride and 2-phenylbenzoyl chloride are reacted with methyl pyrrole-3-carboxylate to yield similar compounds, viz.:

Methyl 5-(4-phenylbenzoyl)pyrrole-3-carboxylate; and
Methyl 5-(2-phenylbenzoyl)pyrrole-3-carboxylate.

EXAMPLE 79

5-(4-Phenylbenzoyl)pyrrole-3-carboxylic Acid

Ethyl 5-(4-phenylbenzoyl)pyrrole-3-carboxylate (3.1 g.) was boiled in an open flask with 100 ml. of methanol and 70 ml. of 1N sodium hydroxide for 1 hour by which time most of the methanol was removed by evaporation. The solution was cooled to room temperature, and product which had precipitated as the sodium salt recovered by filtration. The salt was stirred with 75 ml. of 1N hydrochloric acid and 5-(4-phenylbenzoyl)pyrrole-3-carboxylic acid (1 g., m.p.>280° C.) recovered by filtration.

Analysis: Calcd. for $C_{18}H_{13}O_3N$: C, 74.21; H, 4.50; N, 4.81. Found: C, 73.86; H, 4.61; N, 4.91.

EXAMPLE 80

Methyl 5-Phenylacetylpyrrole-3-carboxylate

Under nitrogen, methyl pyrrole-3-carboxylate (920 mg., 7 mmoles) was dissolved in 25 ml. of methylene chloride. Phenylacetyl chloride (930 mg., 6 mmoles) was added and dissolved. Finally, stannic chloride (1.2 ml., 12 mmoles) was added. The reaction mixture was stirred for 3 hours, water (15 ml.) added dropwise, diluted with 50 ml. of ether, the organic phase separated, washed with 20 ml. of water and evaporated to dryness to yield methyl 5-phenylacetylpyrrole-3-carboxylate (semisolid, Rf 0.3 on silica gel thin layer chromatography with ethyl acetate-1/hexane-5/5% acetic acid as eluant). The entire batch was employed without weight determination in the next step.

EXAMPLE 81

5-Phenylacetylpyrrole-3-carboxylic Acid

All of the methyl 5-phenylacetylpyrrole-3-carboxylate prepared by Example 80 was boiled with methanol (20 ml.) and 1N sodium hydroxide (15 ml.) for 90 minutes. The aqueous residue was cooled, acidified with conc. hydrochloric acid, and crude product (1.2 g.) recovered by filtration. Chromatography on 30 g. of silica gel, employing ethyl acetate-1/hexane-5/5% acetic acid as eluant, gave, on evaporation of the initial, ultraviolet absorbing fractions, purified 5-phenylacetylpyrrole-3-carboxylic acid (470 mg., m.p. 205°–207° C., m/e 229).

Analysis: Calcd. for $C_{13}H_{11}O_3N.0.25H_2O$: C, 67.37; H, 5.00; N, 6.04. Found: C, 66.97; H, 4.99; N, 5.98.

EXAMPLE 82

Methyl 5-Cyclohexylcarbonylpyrrole-3l -carboxylate

To a solution of methyl pyrrole-3-carboxylate (1.25 g., 10 mmoles) in 25 ml. of methylene chloride under nitrogen, was added cyclohexanecarbonyl chloride (1.46 g., 1.33 ml., 10 mmoles) and then stannic chloride (3.13 g., 1.4 ml., 14 mmoles). The resulting solution was stirred 3 hours at room temperature, then 15 ml. of water added slowly and finally 50 ml. of ether. The organic phase was separated, washed with 20 ml. of water, filtered and evaporated to yield methyl 5-cyclohexylcarbonylpyrrole-3-carboxylate (Rf 0.25 on silica gel thin layer chromatography with ethyl acetate-1/hexane-5/5% acetic acid as eluant). The entire batch was used, without weight determination, in the next step.

By the same procedure, cyclopentylcarbonyl chloride and cycloheptylcarbonyl chloride are converted respectively to:
Methyl 5-Cyclopentylcarbonylpyrrole-3-carboxylate; and
Methyl 5-Cycloheptylcarbonylpyrrole-3-carboxylate.

EXAMPLE 83

5-Cyclohexylcarbonylpyrrole-3-carboxylic Acid

The entire batch of methyl 5-cyclohexylcarbonyl-3-carboxylate from Example 82 was hydrolyzed and isolated according to the procedure of Example 81 to yield crude product (1.1 g.). Recrystallization from acetone afforded purified 5-cyclohexylcarbonylpyrrole-3-carboxylic acid (360 mg., m.p. 264°–265° C., m/e 221).

Analysis: Calcd. for $C_{12}H_{15}O_3N$: C, 65.14; H, 6.83; N, 6.33. Found: C, 65.28; H, 6.90; N, 6.46.

By the same procedure the other methyl esters of Example 82 are converted to:
5-Cyclopentylcarbonylpyrrole-3-carboxylic acid; and
5-Cycloheptylcarbonylpyrrole-3-carboxylic acid.

EXAMPLE 84

Methyl 1-Methyl-5-benzoylpyrrole-3-carboxylate

Methyl 5-benzoyl-3-carboxylate (4.1 g., 18 mmoles) was dissolved with stirring in 500 ml. of ether. Sodium hydride (57%, 1.5 g., 36 mmoles) was added and the mixture stirred under nitrogen for 1.5 hours. Dimethylsulfate (3.5 ml., 40 mmoles) was then added and stirring continued for approximately 16 hours. Water (100 ml.) was added slowly, still under nitrogen, and the mixture stirred for 15 minutes. The ether layer was separated, washed with 100 ml. of water and concentrated to dryness to yield methyl 1-methyl-5-benzoyl-3-carboxylate (Rf 0.45 on silica gel thin layer chromatography with ethyl acetate-1/hexane-5/5% acetic acid as eluant). The entire batch of product was used, without weight determination, in the next step.

By the same procedure, other 5-acylpyrrole-3-carboxylic esters prepared in Examples above are converted to:
Methyl 1-methyl-5-(2-methylbenzoyl)pyrrole-3-carboxylate;
Methyl 1-methyl-5-(4-methylbenzoyl)pyrrole-3-carboxylate;
Ethyl 1-methyl-5-(4-chlorobenzoyl)pyrrole-3-carboxylate;
Methyl 1-methyl-5-(2,3-dichlorobenzoyl)pyrrole-3-carboxylate;
Ethyl 1-methyl-5-(4-phenylbenzoyl)pyrrole-3-carboxylate;
Methyl 1-methyl-5-phenylacetylpyrrole-3-carboxylate; and
Methyl 1-methyl-5-cyclohexylcarbonylpyrrole-3-carboxylate.

Belgian Pat. No. 870,910 (published Mar. 29, 1979) discloses preparation of analogous 1-alkyl-5-acylpyrrole-3-carboxylates, specifically exemplifying preparation of methyl 1-methyl-5-(3-chlorobenzoyl)pyrrole-3-carboxylate by Friedel-Crafts acylation of 1-methylpyrrole-3-carboxylic acid followed by esterification and separation from the 4-acyl isomer.

EXAMPLE 85

1-Methyl-5-benzoylpyrrole-3-carboxylic Acid

The entire batch of methyl 1-methyl-5-benzoylpyrrole-3-carboxylate from Example 84 was combined with 200 ml. of ethanol and 100 ml. of 1N sodium hydroxide and refluxed for 2 hours. The ethanol was boiled away, the aqueous residue was cooled to room temperature, extracted with 25 ml. of ether and acidified with conc. hydrochloric acid to yield crystalline product (4 g., m.p. 210°–212° C.). A portion (1.5 g.) was recrystallized from acetone to yield purified 1-methyl-5-benzoylpyrrole-3-carboxylic acid (925 mg., m.p. 215°–216.5° C., m/e 229).

By the same procedure, the other esters of Example 84 are converted to:
1-Methyl-5-(2-Methylbenzoyl)-pyrrole-3-carboxylic acid;
1-Methyl-5-(4-Methylbenzoyl)pyrrole-3-carboxylic acid;
1-Methyl-5-(4-Chlorobenzoyl)pyrrole-3-carboxylic acid;
1-Methyl-5-(2,3-Dichlorobenzoyl)pyrrole-3-carboxylic acid;
1-Methyl-5-(4-Phenylbenzoyl)pyrrole-3-carboxylic acid;
1-Methyl-5-Phenylacetylpyrrole-3-carboxylic acid; and
1-Methyl-5-Cyclohexylcarbonyl-3-carboxylic acid.

Belgian Pat. No. 870,910 (cited above) discloses preparation of analogous 1-alkyl-5-acylpyrrole-3-carboxylic acids, specifically preparation of 1-methyl-5-(3-chlorobenzoyl)pyrrole-3-carboxylic acid by the potassium hydroxide catalyzed hydrolysis of the corresponding methyl ester.

EXAMPLE 86

Ethyl 1-Ethyl-5-benzoylpyrrole-3-carboxylate

Ethyl 5-benzoylpyrrole-3-carboxylate (0.973 g., 4 mmoles) was dissolved in 40 ml. of dry tetrahydrofuran. To the stirred solution, under nitrogen, there was added sodium hydride dispersion in oil (57%, 0.173 g., 4 mmoles), and the mixture was stirred for 0.5 hour. Ethyl iodide (1.25 g., 8 mmoles) was added and stirring continued for 6 hours. Additional sodium hydride (0.17 g.) and ethyl iodide (1.25 g.) was added and reflux continued for an additional 104 hours. Like quantities of sodium hydride and ethyl iodide were added after 16 hours reflux and a like quantity of ethyl iodide after 24 hours reflux. The reaction was cooled and excess sodium hydride decomposed by cautious addition of 40 ml. of water. The product was extracted into 40 ml. of ether, the ether back-washed with 10 ml. of water, and evaporated to dryness to yield ethyl 1-ethyl-5-benzoylpyrrole-3-carboxylate (1 g.), used directly in the next step.

By the same procedure, other 5-acylpyrrole-3-carboxylic esters prepared in Examples above are converted to:
Methyl 1-ethyl-5-(2-methylbenzoyl)pyrrole-3-carboxylate;
Methyl 1-ethyl-(4-methylbenzoyl)pyrrole-3-carboxylate;

Ethyl 1-ethyl-5-(4-chlorobenzoyl)pyrrole-3-carboxylate;
Methyl 1-ethyl-5-(2,3-dichlorobenzoyl)pyrrole-3-carboxylate;
Methyl 1-ethyl-5-(4-phenylbenzoyl)pyrrole-3-carboxylate;
Methyl 1-ethyl-5-phenylacetylpyrrole-3-carboxylate; and
Methyl 1-ethyl-5-cyclohexylcarbonylpyrrole-3-carboxylate.

EXAMPLE 87

1-Ethyl-5-benzoylpyrrole-3-carboxylic Acid

The entire batch of ethyl 1-ethyl-5-benzoylpyrrole-3-carboxylate from the preceding Example was taken up in 40 ml. of methanol and 20 ml. of 1N sodium hydroxide, and heated in an open flask on a steam bath for 1 hour. The aqueous residue was cooled, extracted with 20 ml. of ether, and made acidic with conc. hydrochloric acid. 1-Ethyl-5-benzoylpyrrole-3-carboxylic acid (585 mg., m.p. 157°–158° C., m/e 243) was recovered by filtration. For analysis, the product was recrystallized from acetone/hexane (380 mg., m.p. 158°–160° C.).

Analysis: Calcd. for $C_{14}H_{13}O_3N$: C, 69.12; H, 5.39; N, 5.76. Found: C, 68.90; H, 5.09; N, 5.64.

EXAMPLE 88

Ethyl 4-Methylpyrrole-3-carboxylate

Ethyl 4-methylpyrrole-3-carboxylate was prepared according to the procedure of Cheng et al. [J. Heterocyclic Chem. 13, 1145 (1976)].

EXAMPLE 89

Ethyl 4-Methyl-5-benzoylpyrrole-3-carboxylate

Ethyl 4-methylpyrrole-3-carboxylate (920 mg., 6 mmoles) was combined with benzoyl chloride (0.7 ml., 6 mmoles), stannic chloride (1.2 ml., 12 mmoles) in 25 ml. of methylene chloride and stirred under nitrogen for 2 hours at room temperature. Water (15 ml.) was added slowly, dissolving the precipitate which had formed. Ether (50 ml.) was then added, and the organic phase separated, back-washed with 20 ml. of water, and evaporated to an oil. The oil was triturated with hexane to yield crystalline product (1.12 g.). Recrystallization from acetone/hexane afforded purified ethyl 4-methyl-5-benzoylpyrrole-3-carboxylate (900 mg., m.p. 127°–129° C.).

EXAMPLE 90

4-Methyl-5-benzoylpyrrole-3-carboxylic Acid

Ethyl 4-methyl-5-benzoylpyrrole-3-carboxylate (0.8 g.) was combined with 20 ml. of methanol and 15 ml. of 1N sodium hydroxide and boiled in an open flask for 1.5 hours on a steam bath. The aqueous residue was cooled, extracted with 10 ml. of ether, and acidified with conc. hydrochloric acid to yield crystalline 4-methyl-5-benzoylpyrrole-3-carboxylic acid (630 mg., m.p. 241°–243° C., m/e 229).

Analysis: Calcd. for $C_{13}H_{11}O_3N \cdot 0.125H_2O$: C, 67.45; H, 4.89; N, 6.05. Found: C, 67.18; H, 5.14; N, 5.83.

EXAMPLE 91

Methyl 4-Phenylpyrrole-3-carboxylate p-Tosylmethyl isocyanide (1 g., 5 mmoles) and methyl cinnamate (0.8 g., 5 mmoles) were combined in 50 ml. of tetrahydrofuran and dissolved by stirring at room temperature. The solution was cooled to −50° C. and sodium hydride (57% dispersion in oil, 210 mg., 5 mmoles) added. After stirring for 15 minutes at −50° C., the reaction was warmed to room temperature and stirred for approximately 16 hour. Water (20 ml.) was added and the product extracted into 35 ml. ether. The ether was back-washed with 20 ml. of water, evaporated to dryness, the residue triturated with ether and methyl 4-phenylpyrrole-3-carboxylate (230 mg., m.p. 182°–185° C., m/e 201) recovered by filtration. The product was recrystallized from acetone/hexane (210 mg., m.p. 184°–187° C.).

Analysis: Calcd. for $C_{12}H_{11}O_2N$: C, 71.62; H, 5.51; N, 6.96. Found: C, 71.37; H, 5.55; N, 7.12.

EXAMPLE 92

Methyl 4-Phenyl-5-benzoylpyrrole-3-carboxylate

Methyl 4-phenylpyrrole-3-carboxylate (920 mg., 4.6 mmoles) and benzoyl chloride (0.53 ml., 4.6 mmoles) were combined in 50 ml. methylene chloride and stirred under nitrogen at room temperature. Stannic chloride (1.15 ml., 10 mmoles) was added. The resulting solution was stirred for 1.5 hours. Hydrochloric acid (1N, 25 ml.) was added slowly. The mixture was stirred for 10 minutes, the methylene chloride layer separated, back-washed with two 20 ml. portions of water, approximately 50 mg. of solids removed by filtration, and the filtrate evaporated to dryness. Recrystallization of the residue from acetone afforded purified methyl 4-phenyl-5-benzoylpyrrole-3-carboxylate (673 mg., m.p. 201°–203° C.).

Analysis: Calcd. for $C_{19}H_{15}O_3N$: C, 74.74; H, 4.95; N, 4.59. Found: C, 74.67; H, 4.85; N, 4.51.

EXAMPLE 93

4-Phenyl-5-benzoylpyrrole-3-carboxylic Acid

Methyl 4-phenyl-5-benzoylpyrrole-3-carboxylate (345 mg.) was combined with 20 ml. of methanol and 10 ml. of 1N sodium hydroxide and boiled in an open flask for 1 hour. The aqueous residue was cooled, extracted with ethyl acetate, acidified with conc. hydrochloric acid, and product recovered by filtration. Recrystallization from tetrahydrofuran/hexane afforded purified 4-phenyl-5-benzoylpyrrole-3-carboxylic acid [63 mg., m.p. 285°–287° C. (dec.)].

Analysis: Calcd. for $C_{18}H_{13}O_3N \cdot 0.33H_2O$: C, 72.71; H, 4.63; N, 4.70. Found: C, 72.62; H, 4.52; N, 4.76.

EXAMPLE 94

5-Benzylpyrrole-3-carboxylic Acid

5-Benzoyl-3-carboxylic acid (0.6 g.) was combined with 4 ml. of diethyleneglycol, 2 g. of potassium hydroxide and 1.5 ml. of 97% hydrazine and heated in an oil bath for 1 hour at 135° C. and then 1 hour at 173°–175° C. The reaction mixture was cooled to room temperature, diluted with 30 ml. of water, acidified with conc. hydrochloric acid, and product (350 mg.) recovered by filtration. Recrystallization from ether/hexane afforded purified 5-benzylpyrrole-3-carboxylic acid [160 mg., m.p. 123°–125° C. (turbid), m/e 201].

Analysis: Calcd. for $C_{12}H_{11}O_2N$: C, 71.62; H, 5.51; N, 6.96. Found: C, 71.32; H, 5.55; N, 7.14.

EXAMPLE 95

Methyl 4-Benzoylpyrrole-3-carboxylate

Methyl 3-benzoylacrylate (6.5 g., 33 mmoles) and tosylmethyl isocyanide (6.7 g., 33 mmoles) were dissolved in a mixture of 100 ml. of ether and 40 ml. of dimethylsulfoxide and added dropwise to a suspension of sodium hydride (57% suspension in oil, 2.8 g., 66 mmoles) stirring in 50 ml. of ether, under nitrogen. Addition required 20 minutes, a slightly exothermic reaction being noted. The reaction was stirred for a further 30 minutes at room temperature and diluted with 400 ml. of water. The product was extracted into 150 ml. of ether, the ether back-washed with 250 ml. of water, concentrated to approximately 50 ml., and methyl 4-benzoylpyrrole-3-carboxylate (2.0 g, m.p. 164°–166° C.) recovered by filtration.

Analysis: Calcd. for $C_{13}H_{11}O_3N$: C, 68.11; H, 4.84; N, 6.11. Found: C, 68.00; H, 4.69; N, 6.00.

By the same procedure, methyl 3-(4-methoxybenzoyl)acrylate, methyl 3-(4-methylbenzoyl)acrylate, methyl 3-(3-chlorophenylbenzoyl)acrylate and methyl 3-cyclohexylcarbonyl)acrylate are converted, respectively, to:
Methyl 4-(4-methoxybenzoyl)pyrrole-3-carboxylate;
Methyl 4-(4-methylbenzoyl)pyrrole-3-carboxylate;
Methyl 4-(4-phenylbenzoyl)pyrrole-3-carboxylate;
Methyl 4-(3-chlorobenzoyl)pyrrole-3-carboxylate; and
Methyl 4-cyclohexylcarbonylpyrrole-3-carboxylate.

Belgian Pat. No. 870,910 (published Mar. 29, 1979) generally discloses analogous compounds, specifically examplifying the preparation of methyl 1-methyl-4-(3-chlorobenzoyl)pyrrole-3-carboxylate by Friedel-Crafts acylation of 1-methylpyrrole-3-carboxylate.

EXAMPLE 96

4-Benzoylpyrrole-3-carboxylic Acid

Methyl 4-benzoylpyrrole-3-carboxylate (1 g.) was combined with 30 ml. of methanol and 20 ml. of 1N sodium hydroxide and boiled in an open flask for 1 hour. The aqueous residue was diluted with 20 ml. of water, acidified with concentrated hydrochloric acid, and crystalline 4-benzoylpyrrole-3-carboxylic acid (800 mg., m.p. 220°–222° C.) recovered by filtration.

Analysis: Calcd. for $C_{12}H_9O_3N.0.5H_2O$: C, 64.28; H, 4.49; N, 6.25. Found: C, 64.10; H, 4.05; N, 6.08.

Anhydrous material was obtained by recrystallization from acetone/hexane (m.p. 222°–224° C.).

Analysis: Calcd. for $C_{12}H_9O_3N$: C, 66.97; H, 4.22; N, 6.51. Found: C, 66.86; H, 4.14; N, 6.38.

By the same procedure, the other pyrrole esters of Example 95 are converted to:
4-(4-Methoxybenzoyl)pyrrole-3-carboxylic acid;
4-(4-Methylbenzoyl)pyrrole-3-carboxylic acid;
4-(4-Phenylbenzoyl)pyrrole-3-carboxylic acid;
4-(3-Chlorobenzoyl)pyrrole-3-carboxylic acid; and
4-Cyclohexylcarbonylpyrrole-3-carboxylic acid.

Belgian Pat. No. 870,910 (cited above) generally discloses analogous compounds, specifically exemplifying the preparation of 1-methyl-4-(3-chlorobenzoyl)pyrrole-3-carboxylic acid by potassium hydroxide catalyzed hydrolysis of the corresponding ester.

EXAMPLE 97

Methyl 5-Chloropyrrole-3-carboxylate

Methyl pyrrole-3-carboxylate (2.5 g., 20 mmoles) was dissolved in 50 ml. of methylene chloride. The solution, stirred under nitrogen, was cooled in an ice-water bath while t-butylhypochlorite (1.95 g., 18 mmoles) in 25 ml. of methylene chloride was added dropwise. The reaction was stirred for 1 hour at room temperature, filtered and evaporated to an oil. The oil was chromatographed (100 g. of silica gel with ethyl acetate-1/hexane-7 as eluant). The column elution was monitored by thin layer chromatography (silica gel plates with chloroform-8/ethyl acetate-2 as eluant). Cuts containing pure product (Rf 0.4) were combined and evaporated to yield crystalline methyl 5-chloropyrrole-3-carboxylate (900 mg., m.p. 92°–95° C., m/e 159/161).

EXAMPLE 98

5-Chloropyrrole-3-carboxylic Acid

Methyl 5-chloropyrrole-3-carboxylate (900 g.) was refluxed for 9 hours with 20 ml. of methanol and 10 ml. of 1N sodium hydroxide. Methanol was removed by evaporation, the aqueous residue was diluted with approximately 10 ml. of water and extracted twice with ether. The aqueous phase was acidified with conc. hydrochloric acid and product extracted into ethyl acetate. The three ethyl acetate extracts were combined, washed with saturated sodium chloride, dried over anhydrous sodium sulfate and evaporated to product (715 mg., m.p. 175°–178° C.). Recrystallization from methylene chloride/hexane afforded purified 5-chloropyrrole-3-carboxylic acid (300 mg., m.p. 178°–180° C.).

Analysis: Calcd. for $C_5H_4O_2NC$: C, 41.26; H, 2.76; N, 9.62. Found: C, 41.43; H, 2.87; N, 9.57.

EXAMPLE 99

Methyl 1-Methyl-5-chloropyrrole-3-carboxylate

Methyl 5-chloropyrrole-3-carboxylate (800 mg., 5 mmoles) was dissolved in 75 ml. of ether. Sodium hydride (57% dispersion in oil, 430 mg., 10 mmoles) was added and the mixture stirred under nitrogen for 1 hour. Dimethyl sulfate (1 ml., 10.7 mmoles) was added and stirring continued for 2 hours. Excess sodium hydride was decomposed by cautious addition of 20 ml. of water. The ether phase was washed with 20 ml. of water and evaporated to yield methyl 1-methyl-5-chloropyrrole-3-carboxylate (oil); the entire batch being used directly in the next step.

EXAMPLE 100

1-Methyl-5-chloropyrrole-3-carboxylic Acid

Methyl 1-methyl-5-chloropyrrole-3-carboxylate from the previous example was hydrolyzed in approximately 20 ml. of 1N sodium hydroxide and 30 ml. of ethanol, by boiling on a steam bath for approximately 2 hours. The aqueous residue was diluted with approximately 20 ml. of water, acidified with conc. hydrochloric acid, and crystalline 1-methyl-5-chloropyrrole-3-carboxylic acid recovered by filtration (590 mg., m.p. 201°–203° C.).

Analysis: Calcd. for $C_6H_6O_2NCl$: C, 45.16; H, 3.79; N, 8.78. Found: C, 45.01; H, 3.81; N, 8.66.

EXAMPLE 101

4-Benzylpyrrole-2-carboxylic Acid

4-Benzoylpyrrole-2-carboxylic acid (1.5 g.) was combined with 10 ml. of ethylene glycol, 4 ml. of hydrazine (97%) and 4 g. of potassium hydroxide, and heated for 2 hours in an oil bath maintained at 140°–143° C. The reaction mixture was poured into approximately 100 ml.

of ice and water, acidified with conc. hydrochloric acid, and product (375 mg.) recovered by filtration. Recrystallization from ether/hexane afforded purified 4-benzoylpyrrole-2-carboxylic acid (200 mg., m.p. 183°–185° C.).

Analysis: Calcd. for $C_{12}H_{11}O_2N$: C, 71.62; H, 5.51; N, 6.96. C, 71.52; H, 5.71; N, 7.13.

EXAMPLE 102

2-Hydroxyethyl 4-(4-Chlorophenoxy)pyrrole-2-carboxylate 2-(4-Chlorophenoxy)-3-carbethoxymethylaminoacrylaldehyde (2 g.) was boiled in 5 ml. of ethylene glycol for 15 minutes. The reaction was cooled to room temperature, diluted with 10 ml. of water and product extracted into 10 ml. of ethyl acetate. The ethyl acetate was back-washed with water and concentrated to an oil (1.5 g.). The oil chromatographed on approximately 100 ml. of silica gel with ethyl acetate-1/hexane-1 as eluant, monitored by thin layer chromatography. Evaporation of middle fractions gave ethyl 4-(4-chlorophenoxy)pyrrole-2-carboxylate (100 mg., oil, m/e 281, Rf 0.65 on silica gel thin layer chromatography with ethyl acetate-1/hexane-1/5% acetic acid as eluant; Rf 0.3 with ethyl acetate-1/hexane-1 as eluant). Repeat on a 5.5 g. scale gave an additional 400 mg. of product.

EXAMPLE 103

4-(4-Chlorophenoxy)pyrrole-2-carboxylic Acid

2-Hydroxyethyl 4-(4-chlorophenoxy)pyrrole-2-carboxylate (400 mg.) was dissolved in 10 ml. of acetone and 10 ml. of 1N sodium hydroxide and left to stand at room temperature for approximately 16 hours. Acetone was evaporated in vacuo, the aqueous residue was acidified with conc. hydrochloric acid and crystalline product (320 mg.) recovered by filtration. Recrystallization from ether/hexane of 400 mg. of product prepared in this manner afforded purified 4-(4-chlorophenoxy)pyrrole-2-carboxylic acid (234 mg., m.p. 188°–190° C., m/e 237).

Analysis: Calcd. for $C_{11}H_8O_3NCl$: C, 55.59; H, 3.39; N, 5.89. Found: C, 55.92; H, 3.48; N, 5.82.

EXAMPLE 104

2-Hydroxyethyl 4-(4-Chlorophenyl)pyrrole-2-carboxylate 2-(4-Chlorophenyl)-3-carbethoxymethylaminoacrylaldehyde (73.6 g.) was refluxed in 300 ml. of ethylene glycol for 10 minutes. The reaction mixture was cooled, diluted with 1 liter of water, product extracted into chloroform, treated with activated carbon and evaporated to solids. Trituration with ether gave crude product (8 g.). An additional quantity of crude product (7.5 g.) crystallized from the aqueous phase which had been standing. Recrystallization of the combined crude solids from chloroform gave 2-hydroxyethyl 4-(4-chlorophenyl)pyrrole-2-carboxylate (5 g., m.p. 128°–130° C.). The ether and chloroform mother liquors were combined and evaporated to yield an additional 40 g. of crude product.

EXAMPLE 105

4-(4-Chlorophenyl)pyrrole-2-carboxylic Acid

Crude 2-hydroxyethyl 4-(4-chlorophenyl)pyrrole-2-carboxylate (3 g.) was heated on a steam bath with potassium hydroxide (2 g.) in 25 ml. of water and 25 ml. of ethanol for 30 minutes. The balance of the ethanol was evaporated in vacuo, chloroform (25 ml.) was added and 4-(4-chlorophenyl)pyrrole-2-carboxylic acid (723 mg., m.p. 219°–222° C., ir(KBr): 3390, 3077 and 1695 cm.$^{-1}$, m/e 221/223) recovered by filtration.

EXAMPLE 106

4-Phenylpyrrole-2-carboxylic Acid 4-(4-Chlorophenyl)pyrrole-2-carboxylic acid (0.6 g.) was hydrogenated over 200 mg. of 5% Pd/C in 50 ml. of ethanol for approximately 16 hours at 50 p.s.i. An additional 200 mg. of catalyst and 1 ml. of triethylamine was added and hydrogenation continued for 3 hours at 50 p.s.i. The catalyst was recovered by filtration, and the mother liquor concentrated to dryness to yield 4-phenylpyrrole-2-carboxylic acid [400 mg., m.p. 226°–228° C. (dec.), m/e 187]. For analysis, the product was recrystallized from acetone/hexane [240 mg., m.p. 227°–229° C. (dec.)].

Analysis: Calcd. for $C_{11}H_9O_2N.0.125H_2O$: C, 69.73; H, 4.92; N, 7.39. Found: C, 70.06; H, 4.99; N, 7.26.

EXAMPLE 107

Methyl Pyrrole-2-Carboxylate

Pyrrole-2-carboxylic acid (5 g.) was combined with 200 ml. of methylene chloride and 20 ml. of thionyl chloride and refluxed for 2 hours. The solution was evaporated to dryness in vacuo and the resulting acid chloride converted to ester by addition of 30 ml. of methanol and 20 minutes stirring at room temperature. Ether (50 ml.) was added and the mixture extracted with 50 ml. of water. The ether phase was dried over anhydrous sodium sulfate, filtered and evaporated to yield methyl pyrrole-2-carboxylate (5 g., m.p. 69°–71° C.).

EXAMPLE 108

Methyl 5-Benzoylpyrrole-2-carboxylate

Methylpyrrole-2-carboxylate (1.2 g., 10 mmoles) and benzoyl chloride (1.2 ml., 10 mmoles) were dissolved in 25 ml. of methylene chloride and added, over 2 minutes, to a solution of stannic chloride (2.6 ml., 22 mmoles) in 25 ml. of methylene chloride. After stirring for 2 hours at room temperature, 1N hydrochloric acid (25 ml.) was added slowly and the mixture was stirred for 15 minutes. The methylene chloride phase was separated, back-washed twice with 25 ml. portions of water, and evaporated to yield crude methyl 5-benzoylpyrrole-2-carboxylate (2.3 g.). Chromatography of approximately 3 g. of product prepared in this manner on silica gel with ethyl acetate-1/hexane-2 as eluant, followed by recrystallization of the 2.6 g. thereby obtained from isopropyl alcohol gave 0.75 g. of purified product in two crops (m.p. 111°–113° C.).

Analysis: Calcd. for $C_{13}H_{11}O_3N$: C, 68.11; H, 4.84; N, 6.11. Found: C, 67.80; H, 4.81; N, 6.11.

Alternatively, purified product (5.9 g.) was obtained by fractional crystallization of 18.3 g. of crude from isopropyl alcohol. Also obtained was methyl 4-benzoylpyrrole-2-carboxylic acid (5.2 g., m.p. 135°–137° C.), a compound [Sanchez et al., Carbohydrate Res. 3, 486 (1967)] previously derived from an amino sugar.

By the same procedure, appropriate acid chlorides are reacted with methyl pyrrole-2-carboxylate to yield: Methyl 5-(2-methylbenzoyl)pyrrole-2-carboxylate; Methyl 5-(3-methylbenzoyl)pyrrole-2-carboxylate; Methyl 5-(3-chlorobenzoyl)pyrrole-2-carboxylate;

Methyl 5-(2,5-dichlorobenzoyl)pyrrole-2-carboxylate;
Methyl 5-(3,5-dimethoxybenzoyl)pyrrole-2-carboxylate;
Methyl 5-(4-phenylbenzoyl)pyrrole-2-carboxylate;
Methyl 5-phenylacetylpyrrole-2-carboxylate; and
Methyl 5-cyclohexylcarbonylpyrrole-2-carboxylate.

The preparation of such acids is disclosed broadly in Belgian Pat. No. 870,910, published Mar. 3, 1979. However, no specific compound of this class is described therein.

EXAMPLE 109

5-Benzoylpyrrole-2-carboxylic Acid

Methyl 5-benzoylpyrrole-2-carboxylate (460 mg.) was combined with 10 ml. of methanol and 20 ml. of 1N sodium hydroxide and heated in an open flask on a steam bath for 1 hour. On cooling the aqueous residue, sodium 5-benzoylpyrrole-2-carboxylate (358 mg., m.p. >260° C., thin layer chromatography Rf 0.3 on silica gel with ethyl acetate-1/hexane-5/5% acetic acid as eluant) crystallized and was recovered by filtration. The filtrate was acidified with hydrochloric acid to yield additional product as the free acid [96 mg., m.p. 227°–229° C. (dec.)]. Sodium salt was converted to free acid by stirring in a mixture of 10 ml. of methanol and 20 ml. of 1N hydrochloric acid for 30 minutes [250 mg., m.p. 229°–231° C. (dec)].

Analysis: Calcd. for $C_{12}H_9O_3N$: C, 66.97; H, 4.22; N, 6.51. Found: C, 66.89; H, 4.28; N, 6.49.

By the same procedure, the other esters of Example 108 are converted to:
5-(2-Methylbenzoyl)pyrrole-2-carboxylic acid;
5-(4-Methylbenzoyl)pyrrole-2-carboxylic acid;
5-(4-Chlorobenzoyl)pyrrole-2-carboxylic acid;
5-(2,5-Dichlorobenzoyl)pyrrole-2-carboxylic acid;
5-(3,5-Dimethoxybenzoyl)pyrrole-2-carboxylic acid;
5-(4-Phenylbenzoyl)pyrrole-2-carboxylic acid;
5-Phenylacetylpyrrole-2-carboxylic acid; and
5-Cyclohexylcarbonylpyrrole-2-carboxylic acid.

EXAMPLE 110

Methyl 1-Methyl-5-benzoylpyrrole-2-carboxylate

Under a nitrogen atmosphere, methyl 5-benzoylpyrrole-2-carboxylate (0.85 g., 3.7 mmoles) was dissolved in 175 ml. of ether. To the stirred solution there was added sodium hydride (57% dispersion in oil, 0.31 g., 7.4 mmoles), resulting in a yellow suspension. After stirring for 1 hour at room temperature, dimethylsulfate (0.95 g., 0.7 ml., 7.5 mmoles) was added and the reaction stirred for approximately 16 hours at room temperature. Identically-sized portions of sodium hydride and dimethylsulfate were added, and stirring continued for 8 hours; half quantities of the same reagents were added and stirring continued for an additional 16 hours. The reaction mixture was diluted dropwise with water (20 ml.). The aqueous phase was separated and the organic phase washed with an additional 20 ml. of water. The organic phase was evaporated to dryness to yield solid product contaminated with the oil from the sodium hydride. Recrystallization from methanol gave purified methyl 1-methyl-5-benzoylpyrrole-2-carboxylate (0.78 g., m.p. 111°–113° C., m/e 243).

By the same procedure, the other esters of Example 108 are converted to:
Methyl 1-methyl-5-(2-methylbenzoyl)pyrrole-2-carboxylate;
Methyl 1-methyl-5-(4-methylbenzoyl)pyrrole-2-carboxylate;
Methyl 1-methyl-5-(4-chlorobenzoyl)pyrrole-2-carboxylate;
Methyl 1-methyl-5-(3,5-dichlorobenzoyl)pyrrole-2-carboxylate;
Methyl 1-methyl-5-(3,5-dimethoxybenzoyl)pyrrole-2-carboxylate;
Methyl 1-methyl-5-(4-phenylbenzoyl)pyrrole-2-carboxylate;
Methyl 1-methyl-5-phenylacetylpyrrole-2-carboxylate; and
Methyl 1-methyl-5-cyclohexylcarbonylpyrrole-2-carboxylate.

EXAMPLE 111

1-Methyl-5-benzoylpyrrole-2-carboxylic Acid

Methyl 1-methyl-5-benzoylpyrrole-2-carboxylate (0.78 g.) was heated on a steam bath for 1 hour with 40 ml. of 1N sodium hydroxide and 20 ml. of methanol. The reaction mixture was cooled to room temperature, extracted with ether, made acid with conc. hydrochloric acid and 1-methyl-5-benzoylpyrrole-2-carboxylic acid recovered by filtration (0.47 g., m.p. 178°–181° C.). Recrystallization from acetone/hexane afforded product for analysis (0.34 g., m.p. 178°–180° C.).

Analysis: Calcd. for $C_{13}H_{11}O_3N$: C, 68.11; H, 4.84; N, 6.11. Found: C, 67.82; H, 4.79; N, 6.01.

By the same process, the other esters of Example 110 are hydrolyzed to yield:
1-Methyl-5-(2-methylbenzoyl)pyrrole-2-carboxylic acid;
1-Methyl-5-(4-methylbenzoyl)pyrrole-2-carboxylic acid;
1-Methyl-5-(4-chlorobenzoyl)pyrrole-2-carboxylic acid;
1-Methyl-5-(3,5-dichlorobenzoyl)pyrrole-2-carboxylic acid;
1-Methyl-5-(4-phenylbenzoyl)pyrrole-2-carboxylic acid;
1-Methyl-5-phenylacetylpyrrole-2-carboxylic acid; and
1-Methyl-5-cyclohexylcarbonylpyrrole-2-carboxylic acid.

EXAMPLE 112

1-Methyl-4,5-dibromopyrrole-2-carboxylic Acid

1-Methylpyrrole-2-carboxylic acid (5 g., 40 mmoles) was dissolved in 100 ml. of chloroform. A solution of bromine (2.3 ml., 44 mmoles) in 15 ml. of chloroform was added dropwise over 15 minutes. The reaction mixture was then stirred at room temperature for 1 hour. Additional bromine (2.3 ml., 44 mmoles) was added in one portion. A precipitate formed. More chloroform (50 ml.) was added and stirring continued for 20 minutes. 1-Methyl-4,5-dibromopyrrole-2-carboxylic acid was recovered by filtration [5 g., m.p. 173°–175° C. (dec.), m/e 283]. One gram of product was recrystallized from 1 to 1 acetone-water [614 mg., m.p. 180°–182° C. (dec.)].

EXAMPLE 113

Sodium 5-Phenylthiopyrrole-3-carboxylate

5-Phenylthiopyrrole-3-carboxylate is combined with an equivalent of sodium ethoxide in ethyl acetate. Sodium 5-phenylthiopyrrole-3-carboxylate is isolated by concentration to dryness or by precipitation resulting from addition of a non-solvent (ether or hexane).

Substitution of an equivalent amount of diethanol amine for sodium ethoxide is employed to produce diethanolammonium 5-phenylthio-3-carboxylate.

EXAMPLE 114

Potassium 5-Butylthiopyrrole-3-carboxylate

5-Butylthiopyrrole-3-carboxylate is dissolved in ethyl acetate. An equivalent of ethanolic potassium hydroxide is added. Potassium 5-butylthiopyrrole-3-carboxylate is isolated by concentration to dryness or by precipitation resulting from addition of a non-solvent (ether or heptane).

Substitution of an equivalent of N-methylglucamine (meglumine) for the ethanolic potassium hydroxide is employed to produce N-methylglucammonium 5-butylthiopyrrole-3-carboxylate.

EXAMPLE 115

Sodium 1-Methyl-5-benzoylpyrrole-3-carboxylate

1-Methyl-5-benzoylpyrrole-3-carboxylate is dissolved by warming in acetone. An equivalent of sodium methoxide is added with stirring. Sodium 1-methyl-5-benzoylpyrrole-3-carboxylate is isolated by evaporation to dryness or by precipitation resulting from addition of a non-solvent (ether or pentane).

Substitution of a molar equivalent of piperazine for sodium methoxide is employed to produce piperazinium 1-methyl-5-benzoylpyrrole-3-carboxylate.

EXAMPLE 116

Magnesium 4-(4-Chlorophenoxy)pyrrole-2-carboxylate 4-(4-Chlorophenoxy)pyrrole-2-carboxylate and an equivalent quantity of magnesium oleate are each dissolved in ethanol and the solutions mixed. Magnesium 4-(4-chlorophenoxy)pyrrole-2-carboxylate is isolated by concentration and/or addition of heptane.

Substitution of an equivalent of calcium palmitate for magnesium oleate in this process is employed to produce calcium 4-(4-chlorophenoxy)pyrrole-2-carboxylate.

EXAMPLE 117

Salt Formation

Alternatively, the acid products of Examples 1 to 112 are converted to the sodium, potassium, ammonium, calcium, magnesium, aluminum, triethylamine, tri-n-butylamine, piperidine, triethanolamine, diethylaminoethylamine, pyrrolidine and N,N-dibenzylethylenediamine salts by reaction with an equivalent of the appropriate metal hydroxide, ammonium hydroxide or amine in water or ethanol followed by filtration of the salt if it is insoluble or by evaporation of the solvent if the salt is soluble therein.

EXAMPLE 118

Capsules

A blend is prepared containing the following ingredients in the proportion by weight indicated:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient sodium 5-phenylthiopyrrole-3-carboxylate to fill standard size capsules so as to contain 500 mg., 300 mg., 100 mg., 50 mg. or 25 mg. of 5-phenylthiopyrrole-3-carboxylic acid. The portion of blend to active drug is within the limits of 1–0.1 to 1–2, i.e., 27.8 mg. of sodium salt and 250 mg. of blend in a 25 mg. carpsule or 556 mg. of sodium salt and 250 mg. of blend in a 500 mg. capsule as examplary of the extremes.

EXAMPLE 119

Tablets

A tablet base is prepared by blending the following ingredients in the proportion by weight indicated:

| | |
|---|---|
| Sucrose, U.S.P. | 80.3 |
| Tapioca Starch | 13.2 |
| Magnesium Stearate | 6.5 |

Into this tablet base there is blended sufficient sodium 1-methyl-5-benzoylpyrrole-3-carboxylate to form tablets containing 50 mg., 100 mg or 250 mg. of 1-methyl-5-benzoylpyrrole-3-carboxylic acid. The portion of blend to active drug is within the limits of 1–0.167 to 1–1, i.e., 54.8 mg. of sodium salt and 300 mg. of blend in a 50 mg. tablet or 274 mg. of sodium salt and 250 mg. of blend in a 250 mg. tablet.

EXAMPLE 120

Injectable Preparation

A solution for parenteral, especially intramuscular injection is prepared with the following composition:

| | |
|---|---|
| Magnesium 4-(4-chlorophenoxy)-pyrrole-3-carboxylate | 6.35 g.* |
| Magnesium chloride hexahydrate | 12.36 g. |
| Monoethanolamine | 8.85 g. |
| Propylene glycol | 376.00 g. |
| Water, distilled | 94.00 g. |

*Weight equivalent to 6.04 g. 4-(4-chlorophenoxy)pyrrole-3-carboxylate.

The resultant solution has a concentration of effective ingredient of 10 mg./ml.

EXAMPLE 121

Injectable Preparation

One hundred grams of sterile 5-(4-phenylbenzoyl)-pyrrole-3-carboxylic acid is blended with 250 g. of sterile sodium ascorbate. The blend is dry filled into vials such that each vial contains 55 mg. of the active ingredient. Immediately before use, 11 ml. of sterile water for injection is added to give a 5 mg./ml. solution suitable for intravenous injection.

PREPARATION 1

2,4-Dichlorothiophenol

Following the procedure of French Pat. No. 1,481,052 [Chem. Abstr. 69, 18840h (1968)], 2,4-dichloroaniline (32.4 g., 0.2 mole) was added to a mixture of 200 ml. of conc. hydrochloric acid and approximately 200 g. of ice. The mixture was stirred at room temperature for 30 minutes; complete dissolution did not occur. The mixture was cooled to −2° C. and a solution of 15.2 g. of sodium nitrite (0.22 mole) in 50 ml. of water was added over a 10 minute period, maintaining the temperature between −2° and 2° C. during the addition. The reaction was stirred at 0°–2° C. for 30 minutes. Almost complete dissolution had occurred. This cold solution was added portionwise over 15 minutes to a solution of potassium ethylxanthate (35.2 g., 0.22 mole) in 100 ml. of water, maintained at 45°–50° C. Heating at 50°–55° C. was continued for 30 minutes after addition was complete. The reaction was cooled to room temperature and the intermediate extracted into 200 ml. of ether. The ether phase was back-washed with water (150 ml.), with 1N sodium hydroxide and twice more with 150 ml. portions of water, and concentrated to yield 2,5-dichlorophenyl ethylxanthate (33 g. as an oil).

Without further purification the xanthate intermediate was combined with 200 ml. of absolute ethanol and heated to reflux. Potassium hydroxide (85% pure, 12 g., 0.18 mole) was added in small portions over 30 minutes. Reflux was continued for 2 hours. After cooling to room temperature, the reaction mixture was filtered to remove insoluble byproducts. To the filtrate was added 500 ml. of water, 200 ml. of ether and 100 ml. of hexane. The organic phase was separated and extracted with 500 ml. of 0.5N sodium hydroxide. The combined aqueous phases were acidified with conc. hydrochloric acid and the product extracted into 150 ml. ether. The ether extract was back-washed with water, dried over anhydrous sodium sulfate and evaporated in vacuo to yield 2,4-dichlorothiophenol (6.7 g.) as an oil.

PREPARATION 2

2,5-Dichlorothiophenol

Following the procedure of Preparation 1, 3,5-dichloroaniline (32.4 g., 0.2 mole) was reacted with sodium nitrite and then potassium ethylxanthate to form intermediate 3,5-dichlorophenyl ethylxanthate (25.5 g.). The latter was hydrolyzed and 3,5-dichlorothiophenyl (11.4 g.) isolated following the further procedures of Preparation 1.

PREPARATION 3

Dicyclohexyl Disulfide

By the method of Frank and Blegen [Org. Syntheses 28, 16 (1948)], cyclohexyl mercaptan is oxidized by the action of hydrogen peroxide to dicyclohexyl disulfide.

PREPARATION 4

Acid Chlorides

Acid chlorides required for use in various Examples of this patent are prepared by reaction of the corresponding acid (10 g.) with an equivalent of thionyl chloride in refluxing methylene chloride (100 ml.) for 2 hours in the presence of a catalytic amount of dimethylformamide (0.1 ml.). The acid chlorides are isolated by evaporation to dryness in vacuo, and are purified by distillation, if necessary. In this manner, the following acid chlorides are prepared:
Cyclopentanecarbonyl chloride;
Cyclohexanecarbonyl chloride;
Cycloheptanecarbonyl chloride;
2-Phenylbenzoyl chloride;
4-Phenylbenzoyl chloride.

PREPARATION 5

2-Formamidomethylpyridine

2-Aminomethylpyridine (60 g.) was refluxed with 180 ml. of formic acid for 4 hours and left to stir for approximately 16 hours at room temperature. The reaction mixture was concentrated to an oil and purified; 2-formamidomethylpyridine obtained by distillation (72.3 g., b.p. 117°–141° C./0.5 mm.)

PREPARATION 6

Imidazo[3,4-a]pyridine

2-Formamidomethylpyridine (39 g., 0.29 mole) was dissolved in 150 ml. of benzene. Phosphorus oxychloride (100 ml.) was added dropwise at such a rate that the reaction began to reflux. By external heating, reflux was maintained for 3.5 hours. After standing approximately 16 hours at room temperature, the reaction was concentrated to an oil. The oil was poured onto approximately 300 g. of ice, the mixture made basic (approximately pH 10) with 10N sodium hydroxide, and extracted with three 300 ml. portions of methylene chloride. The aqueous was made more basic and extracted with a further three 300 ml. portions of methylene chloride. All of the extracts were combined, back-washed with 75 ml. of water and concentrated to yield crystalline imidazo[3,4-a]pyridine (29 g., Rf 0.25 on thin layer chromatography on silica gel with ethyl acetate/5% acetic acid as eluant).

PREPARATION 7

Methyl 3-Benzoylacrylate

3-Benzoylacrylic acid (3 g.) was refluxed for 2 hours with 100 ml. of methylene chloride and 10 ml. thionyl chloride. Concentration to dryness gave 3-benzoylacrylyl chloride. Methanol (15 ml.) was added and the resulting solution stirred for 0.5 hour. Ether (35 ml.) was added. The resulting organic mixture was washed in sequence with 15 ml. of water, 15 ml. of 1N sodium hydroxide and twice with 15 ml. of water, concentrated to an oil, the oil triturated with 25 ml. of hot hexane, decanted from insolubles and the hexane concentrated to yield methyl 3-benzoylacrylate (1.9 g., oil, m/e 190).

By the same procedure, 3-(4-methoxybenzoyl)acrylic acid 3-(4-methylbenzoyl)acrylic acid, 3-(4-phenylbenzoyl)acrylic acid and 3-(3-chlorobenzoyl)acrylic acid are reacted with sulfonyl chloride and then methanol to form, respectively:
Methyl 3-(4-methoxybenzoyl)acrylate;
Methyl 3-(4-methylbenzoyl)acrylate;
Methyl 3-(4-phenylbenzoyl)acrylate;
Methyl 3-(3-chlorophenylbenzoyl)acrylate; and
Methyl 3-(cyclohexylcarbonyl)acrylate.

Those acylacrylic acids not available commercially are prepared by acylation of the appropriate benzene derivative with maleic anhydride [see Grummitt et al. Org. Syn. III, 109 (1955)], condensation of the appropriate methyl ketone with chloral, followed by hydrolysis and dehydration [see Koenigs and Wagstaffe, Ber 26, 558 (1893)], or halogenation of the appropriate 3-acylpropionic acid followed by dehydrohalogenation [see Bougault, Ann. Chim. Phys. 15, 491 (1908)].

PREPARATION 8

4-Chlorophenoxyacetaldehyde Diethylacetal

Potassium hydroxide (56.1 g., 1 mole) was added slowly to 4-chlorophenol (128.5 g., 1 mole) and the mixture heated to obtain a solution. Chloroacetaldehyde (300 g.) was added over 30 minutes from a dropping funnel and the mixture refluxed for approximately 16 hours (temperature approximately 175° C.). The reaction mixture was cooled to room temperature, diluted with approximately 300 ml. of water, product extracted into ether (three 200 ml. portions), the ether dried over anhydrous sodium sulfate, and the ether evaporated to an oil. Distillation of the oil afforded purified 4-chlorophenoxyacetaldehyde diethylacetal (144.8 g., b.p. 158°–163° C./20 mm.)

PREPARATION 9

2-(4-Chlorophenoxy)-3-dimethylaminoacrylaldehyde

Dimethylformamide (109.5 g., 1.5 moles) was cooled in an ice-water bath. Phosphorus oxychloride (229.5 g., 1.5 moles) was added dropwise over 1.5 hours and the reaction mixture then allowed to stir for 45 minutes at room temperature. Chloroform (300 ml.) was added and then 4-chlorophenoxyacetaldehyde dimethylacetal (122 g., 0.5 moles) and the mixture refluxed for approximately 16 hours. The reaction was cooled to room temperature and added slowly to approximately 300 ml. of chloroform mixed with ice and water while maintaining the pH approximately 10 with sodium hydroxide. Aqueous 40% dimethylamine (400 ml.) was added, the organic layer separated and the aqueous extracted with additional chloroform. The chloroform extracts were combined, dried over anhydrous sodium sulfate, concentrated to a semisolid, and crystalline product recovered by trituration with isopropyl ether (95 g., Rf 0.25 on thin layer chromatography on silica gel with ethyl acetate as eluant).

PREPARATION 10

2-(4-Chlorophenoxy)-3-carbethoxymethylaminoacrylaldehyde 2-(4-Chlorophenoxy)-3-dimethylaminoacrylaldehyde (11.3 g., 50 mmoles) was dissolved in 200 ml. of ethanol, mixed with a solution of ethyl glycinate (14 g., 100 mmoles) in 90 ml. of 1N sodium hydroxide and refluxed for 15 hours. Ethanol was evaporated in vacuo, the aqueous residue diluted with 150 ml. of water and product extracted into 200 ml. of ethyl acetate. The ethyl acetate was back-washed with water and concentrated to an oil. Trituration of the oil with 100 ml. of ether gave crystalline 2-(4-chlorophenoxy)-3-carbethoxymethylaminoacrylaldehyde in two crops (7.3 g., Rf 0.55 on silica gel thin layer chromatography with ethyl acetate-1/hexane-1/5% acetic acid as eluant).

PREPARATION 11

2-(4-Chlorophenyl)-3-dimethylaminoacrylaldehyde

Phosphorus oxychloride (218 g., 2.18 moles) was added dropwise to dimethylformamide (157 ml., 2.28 moles), maintaining the temperature at 25° C. 4-Chlorophenylacetic acid (130.6 g., 0.76 mole), dissolved in a mixture of 400 ml. of chloroform and 25 ml of dimethylformamide, was added in a stream and the reaction refluxed for approximately 16 hours. The reaction was cooled to room temperature and poured slowly into ice and water, while maintaining the pH approximately 10 with sodium hydroxide. Dimethylamine (500 ml. of 25% aqueous) was then added and the mixture heated on the steam bath for 1 hour. The mixture was cooled, extracted with four 500 ml. portions of chloroform, the chloroform extracts combined, dried over anhydrous sodium sulfate, treated with activated carbon and evaporated to an oil. Trituration with cold isopropyl ether gave crystalline 2-(4-chlorophenyl)-3-dimethylaminoacrylaldehyde (111 g., Rf 0.25 on silica gel thin layer chromatography with ethyl acetate as eluant).

PREPARATION 12

2-(4-Chlorophenyl)-3-carbethoxymethylaminoacrylaldehyde 2-(4-Chlorophenyl)-3-dimethylaminoacrylaldehyde (90.2 g., 0.43 mole) was dissolved in 1500 ml. of ethanol. Ethyl glycinate hydrochloride (60.2 g., 0.86 mole) was dissolved in 900 ml. of water and the pH adjusted to 7.5 with 6N sodium hydroxide. The solutions were combined and refluxed for 6 hours. The ethanol was removed by evaporation, the product extracted into chloroform, the chloroform dried over anhydrous sodium sulfate, evaporated to dryness, the solid residue triturated with ether and crystalline 2-(4-chlorophenyl)-3-carbethoxymethylaminoacrylaldehyde (73.6 g., m.p. 84°–86° C.) recovered by filtration.

I claim:

1. A method of lowering the level of blood glucose in a hyperglycemic mammal which comprises administering to said hyperglycemic mammal a compound selected from the group of pyrrole carboxylic acids consisting of:

4,5-bis(4-methoxyphenylthio)pyrrole-3-carboxylic acid;
1-methyl-4,5-bis(phenylthio)pyrrole-2-carboxylic acid;
4-methyl-5-benzoylpyrrole-3-carboxylic acid;
4-phenyl-5-benzoylpyrrole-3-carboxylic acid;
4-bromo-5-benzoylpyrrole-2-carboxylic acid;
5-bromo-4-benzoylpyrrole-2-carboxylic acid; and
1-methyl-4,5-dibromopyrrole-2-carboxylic acid;
or a pharmaceutically-acceptable salt thereof, in an amount sufficient to lower said blood glucose level in said hyperglycemic mammal.

2. A method of lowering the level of blood glucose in a hyperglycemic mammal which comprises administering to said hyperglycemic mammal a compound selected from the group of pyrrole carboxylic acids consisting of 4,5-bis(4-methoxyphenylthio)pyrrole-3-carboxylic acid, 1-methyl-4,5-bis(phenylthio)pyrrole-2-carboxylic acid and pharmaceutically acceptable salts thereof, in an amount sufficient to lower said blood glucose level in said hyperglycemic mammal.

3. The method of claim 2 wherein the compound is 1-methyl-4,5-bis(phenylthio)pyrrole-2-carboxylic acid.

4. A compound selected from the group of pyrrole carboxylic acids consisting of 4,5-bis(4-methoxyphenylthio)pyrrole-3-carboxylic acid, 1-methyl-4,5-bis(phenylthio)pyrrole-2-carboxylic acid, the pharmaceutically acceptable salts thereof, and the $C_1$ to $C_3$ alkyl esters thereof.

5. The compound of claim 4 which is 1-methyl-4,5-bis(phenylthio)pyrrole-2-carboxylic acid.

* * * * *